(12) United States Patent
Szymkiewicz et al.

(10) Patent No.: US 11,890,099 B2
(45) Date of Patent: *Feb. 6, 2024

(54) SYSTEMS AND METHODS OF PATIENT DATA COMPRESSION

(71) Applicant: ZOLL Medical Corporation, Chelmsford, MA (US)

(72) Inventors: Steven J. Szymkiewicz, Bethel Park, PA (US); Francesco Nicolo, Oakmont, PA (US); Gary A. Freeman, Waltham, MA (US); Timothy F. Stever, Lowell, MA (US); Shane S. Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/744,013

(22) Filed: May 13, 2022

(65) Prior Publication Data

US 2022/0265195 A1 Aug. 25, 2022

Related U.S. Application Data

(60) Continuation of application No. 16/929,920, filed on Jul. 15, 2020, now Pat. No. 11,357,436, which is a
(Continued)

(51) Int. Cl.
*A61B 5/316* (2021.01)
*A61B 5/00* (2006.01)
(Continued)

(52) U.S. Cl.
CPC ............ *A61B 5/316* (2021.01); *A61B 5/0006* (2013.01); *A61B 5/0022* (2013.01);
(Continued)

(58) Field of Classification Search
CPC .... A61N 1/3904; A61N 1/025; A61N 1/0456; A61N 1/046; A61N 1/365; A61N 1/3704;
(Continued)

(56) References Cited

U.S. PATENT DOCUMENTS 5,400,371 A * 3/1995 Natarajan ................ H04B 1/62
375/240
5,570,305 A 10/1996 Fattouche et al.
(Continued)

FOREIGN PATENT DOCUMENTS

EP 0761255 A1 3/1997

*Primary Examiner* — Catherine M Voorhees
*Assistant Examiner* — Roland Dinga
(74) *Attorney, Agent, or Firm* — FINCH & MALONEY PLLC

(57) ABSTRACT

A system including a medical device is provided. The medical device includes at least one sensor configured to acquire first data descriptive of a patient, first memory storing a plurality of templates, and at least one processor coupled to the at least one sensor and the first memory. The at least one processor is configured to identify a first template of the plurality of templates that is similar to the first data, to determine first difference data based on the first template and the first data, and to store the first difference data in association with the first template. The system may further include the programmable device.

20 Claims, 14 Drawing Sheets

Related U.S. Application Data division of application No. 15/474,424, filed on Mar. 30, 2017, now Pat. No. 10,750,966.

(60) Provisional application No. 62/316,087, filed on Mar. 31, 2016.

(51) Int. Cl.

| | | |
|---|---|---|
| *A61N 1/02* | (2006.01) | |
| *A61N 1/04* | (2006.01) | |
| *A61N 1/365* | (2006.01) | |
| *A61N 1/37* | (2006.01) | |
| *A61N 1/39* | (2006.01) | |
| *A61B 5/0205* | (2006.01) | |
| *A61B 5/318* | (2021.01) | |
| *A61B 5/349* | (2021.01) | |
| *A61B 5/369* | (2021.01) | |

(52) U.S. Cl.
CPC ............ *A61B 5/0205* (2013.01); *A61B 5/318* (2021.01); *A61B 5/349* (2021.01); *A61B 5/369* (2021.01); *A61B 5/6804* (2013.01); *A61B 5/6805* (2013.01); *A61B 5/7232* (2013.01); *A61B 5/7465* (2013.01); *A61N 1/025* (2013.01); *A61N 1/046* (2013.01); *A61N 1/0456* (2013.01); *A61N 1/365* (2013.01); *A61N 1/3704* (2013.01); *A61N 1/3904* (2017.08); *A61N 1/3975* (2013.01); *A61N 1/3993* (2013.01)

(58) Field of Classification Search
CPC .... A61N 1/3975; A61N 1/3993; A61B 5/316; A61B 5/369; A61B 5/349; A61B 5/318; A61B 5/0006; A61B 5/0022; A61B 5/0205; A61B 5/6804; A61B 5/6805; A61B 5/7232; A61B 5/7465
See application file for complete search history.

(56) References Cited

U.S. PATENT DOCUMENTS

| | | | |
|---|---|---|---|
| 5,657,398 A * | 8/1997 | Guilak | A61B 5/7232 |
| | | | 382/128 |
| 5,772,604 A | 6/1998 | Landberg et al. | |
| 6,320,590 B1 | 11/2001 | Go | |
| 7,091,981 B2 | 8/2006 | Go | |
| 7,500,955 B2 | 3/2009 | Sweeney | |
| 7,715,905 B2 | 5/2010 | Kurzweil et al. | |
| 8,280,508 B2 | 10/2012 | Sweeney | |
| 8,868,165 B1 * | 10/2014 | Nabutovsky | A61B 5/7246 |
| | | | 600/515 |
| 8,983,587 B2 | 3/2015 | Kurzweil et al. | |
| 9,161,723 B2 | 10/2015 | Rodriguez-Llorente et al. | |
| 9,179,851 B2 | 11/2015 | Baumann et al. | |
| 9,326,734 B1 * | 5/2016 | Chai | H03M 7/30 |
| 11,357,436 B2 * | 6/2022 | Szymkiewicz | A61N 1/3975 |
| 2004/0267143 A1 | 12/2004 | Sweeney | |
| 2007/0016029 A1 | 1/2007 | Donaldson et al. | |
| 2009/0192395 A1 | 7/2009 | Sweeney | |
| 2013/0172763 A1 * | 7/2013 | Wheeler | A61B 5/7221 |
| | | | 600/509 |
| 2014/0073982 A1 | 3/2014 | Yang et al. | |
| 2016/0278659 A1 * | 9/2016 | Kaib | A61B 5/361 |
| 2017/0156678 A1 * | 6/2017 | Lim | A61B 5/316 |
| 2018/0263511 A1 | 9/2018 | Burnes et al. | |

\* cited by examiner

SYSTEMS AND METHODS OF PATIENT DATA COMPRESSION

RELATED APPLICATIONS

This application claims the benefit under 35 U.S.C. § 120 as a continuation of U.S. patent application Ser. No. 16/929,920, titled "SYSTEMS AND METHODS OF PATIENT DATA COMPRESSION," filed on Jul. 15, 2020, which claims the benefit under 35 U.S.C. § 121 as a division of U.S. patent application Ser. No. 15/474,424, titled "SYSTEMS AND METHODS OF PATIENT DATA COMPRESSION," filed on Mar. 30, 2017, which claims priority under 35 U.S.C. § 119 (e) to U.S. Provisional Application Ser. No. 62/316,087, titled "SYSTEMS AND METHODS OF PATIENT DATA COMPRESSION," filed Mar. 31, 2016, each of which is hereby incorporated herein by reference in its entirety for all purposes.

BACKGROUND

This disclosure relates generally to medical devices, and more specifically, to apparatus and processes that compress and decompress data acquired by medical devices that is descriptive of patient activity.

Conventional medical devices generate a large volume of data descriptive of patient activity. Examples of this data include electrocardiogram (ECG) data, electroencephalogram (EEG) data, heart sounds data, heartrate data, respiration data, blood oxygen level data, body temperature data, patient location data, patient orientation data, and other patient data. The transmission and storage of this patient data can consume substantial computing resources. For example, 24 hours of 12 lead ECG data can consume as much as 1 to 2 gigabytes.

SUMMARY

Some forms of home-based, and other out-of-hospital medical monitoring may require real-time transmission of patient data, such as physiologic data, from remote locations over communication channels with limited data bandwidth. In situations like these and others, medical personnel may need to review the patient data and provide diagnoses rapidly, within seconds, in order to save patients' lives. Uncompressed physiologic data transmission over limited bandwidth communication channels may result in substantial delays (e.g., several minutes to as much as half an hour) in reception of the transmitted physiologic data. Delays in the review of such data by medical personnel increase risks of patient disability and mortality. In addition, the aggregation or transmission of data collected during a home-based or other out-of-hospital event may require supervision or monitoring throughout the duration of the data transfer, which delays the availability of personnel and equipment and increases the costs associated with such data transfers.

To address these and other concerns, examples disclosed herein implement techniques that make efficient use of communication channels that transport patient data. For instance, some examples are directed to systems and methods that limit transmission of forms of patient data that require relatively high bandwidth (e.g., high resolution data) by instead transmitting forms of patient data that require relatively low bandwidth (e.g., low resolution data). In some of these examples, the systems and methods transmit low resolution data, receive guidance that indicates particular portions of high resolution data to transit, and transmit only those portions. In these examples, the guidance may be received from user input that is informed by the low resolution data. Alternatively or additionally, some examples disclosed herein compress patient data to decrease the bandwidth required to transmit and/or store the patient data. In these examples, components may refer to one or more templates to increase compression effectiveness.

In one example, a system including a medical device is provided. The medical device includes at least one sensor configured to acquire first data descriptive of a patient, first memory storing a plurality of templates, and at least one processor coupled to the at least one sensor and the first memory. The at least one processor is configured to identify a first template of the plurality of templates that is similar to the first data, to determine first difference data based on the first template and the first data, and to store the first difference data in association with the first template.

In the system the at least one processor may be configured to compress the first difference data to generate compressed difference data and to transmit the compressed difference data to a programmable device distinct from the medical device.

The system may further include the programmable device. The programmable device may include second memory storing the plurality of templates and one or more processors coupled to the second memory. The one or more processor may be configured to receive the compressed difference data and an identifier of the first template from the medical device, to decompress the compressed difference data to generate a copy of the first difference data, to retrieve a copy of the first template from the plurality of templates stored in the second memory, and to reconstruct a copy of the first data using the copy of the first template and the copy of the first difference data.

In the system, the at least one sensor may be configured to acquire second data descriptive of the patient. The at least one processor may be configured to identify a second template of the plurality of templates that is similar to the second data, to determine second difference data based on the second template and the second data, and to store the second difference data in association with the second template.

In another example, a medical device is provided. The medical device includes at least one sensor configured to acquire first and second data descriptive of a patient, memory storing a plurality of templates, and at least one processor coupled to the at least one sensor and the memory. The at least and configured to identify first and second templates of the plurality of templates that are respectively similar to the first and second data, to determine first and second difference data sets based on the first template and the first data set and the second template and the second data set respectively, and to store the first and second difference data sets in association with the first and second templates.

In another example, a system including a medical device is provided. The system includes at least one sensor configured to acquire high resolution data descriptive of a patient, at least one network interface, and at least one processor coupled to the at least one sensor and the at least one network interface. The at least one processor is configured to transmit low resolution data descriptive of the high resolution data on a first data stream, to receive, via the first data stream, an indication of a portion of low resolution data of interest, and to transmit high resolution data covering the portion via a second data stream.

The system may further include a programmable device configured to receive the low resolution data from the medical device via the first data stream, to present the low resolution data to a user, to receive the indication of the portion from the user, and to transmit the indication of the portion to the medical device via the first data stream. The programmable device may be configured to receive the high resolution data from the medical device via the second data stream and to supplement the low resolution data with the high resolution data.

In another example, a system including a medical device is provided. The system includes at least one sensor configured to acquire first and second data descriptive of a patient, at least one network interface, and at least one processor coupled to the at least one sensor and the at least one network interface. The at least one processor is configured to store the first data descriptive of the patient, to calculate difference data between the first data and the second data, and to store the difference data in association with the first data.

In the system, the at least one processor may be configured to compress the first data and the difference data to generate compressed data and to transmit the compressed data to a programmable device distinct from the medical device.

The system may further include the programmable device. The programmable device may be configured to receive the compressed data, decompress the compressed data to generate a copy of the first data and a copy of the difference data and to reconstruct a copy of the second data using the copy of the first data and the copy of the difference data.

In the system, the at least one processor may be configured to reconstruct the second data into patched data using the first data and the difference data, to calculate an amount of error based on the second data and the patched data, to compress the first data and the second data to generate compressed data in response to detecting that the amount of error exceeds a threshold, and to transmit the compressed data to the programmable device.

In another example, a system including a medical device is provided. The system includes at least one first sensor configured to acquire first data descriptive of a patient condition, at least one second sensor configured to acquire second data descriptive of the patient condition, at least one network interface, and at least one processor coupled to the at least one first sensor, the at least one second sensor, and the at least one network interface and configured to calculate difference data between the first data and the second data, and to store the difference data in association with the first data.

In the system, the at least one processor may be configured to compress the first data and the difference data to generate compressed data and to transmit the compressed data to a programmable device distinct from the medical device.

The system may further include the programmable device. The programmable device may be configured to receive the compressed data, to decompress the first data to generate a copy of the first data and a copy of the difference data, and to reconstruct a copy of the second data using the copy of the first data and the copy of the difference data. The system may further include at least one third sensor configured to acquire third data descriptive of the patient condition, and the at least one processor may be configured to downsample at least a portion of the third data and to store the third data in association with the first data and the second data. The first data may include electrocardiogram (ECG) data, the second data may include ECG data, and the third data may include heart sounds data.

In the system, the at least one first sensor may be configured to acquire third data descriptive of at least one other patient condition, to calculate additional difference data between the first data and the third data, and to store the additional difference data in association with the first data. The system may further include a programmable device configured to receive the first data, the difference data, and the additional difference data, to reconstruct a copy of the second data using the received first data and the received difference data, and to reconstruct a copy of the third data using the received first data and the received additional difference data. The first data and the third data may include electrocardiogram (ECG) data.

The system may further include a memory storing a plurality of templates. The at least one processor may be coupled to the memory and may be configured to identify a template of the plurality of templates that is similar to the first data, determine additional difference data between the template and the first data, and store the additional difference data in association with the template. The system may further include a programmable device including second memory storing the plurality of templates and one or more processors coupled to the second memory. The one or more processors may be configured to receive the difference data, the additional difference data, and an identifier of the template from the medical device, to retrieve a copy of the template from the plurality of templates stored in the second memory, to reconstruct a copy of the first data using the copy of the template and the received additional difference data, and to reconstruct a copy of the second data using the copy of the first data and the received difference data. The at least one processor of the medical device may be configured to transmit the difference data, the additional difference data, and the identifier of the template to the programmable device.

Still other aspects, examples and advantages of these aspects and examples, are discussed in detail below. Moreover, it is to be understood that both the foregoing information and the following detailed description are merely illustrative examples of various aspects and features, and are intended to provide an overview or framework for understanding the nature and character of the claimed aspects and examples. Any example or feature disclosed herein may be combined with any other example or feature. References to different examples are not necessarily mutually exclusive and are intended to indicate that a particular feature, structure, or characteristic described in connection with the example may be included in at least one example. The appearances of such terms herein are not necessarily all referring to the same example.

DESCRIPTION OF DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended as a definition of the limits of any particular example. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
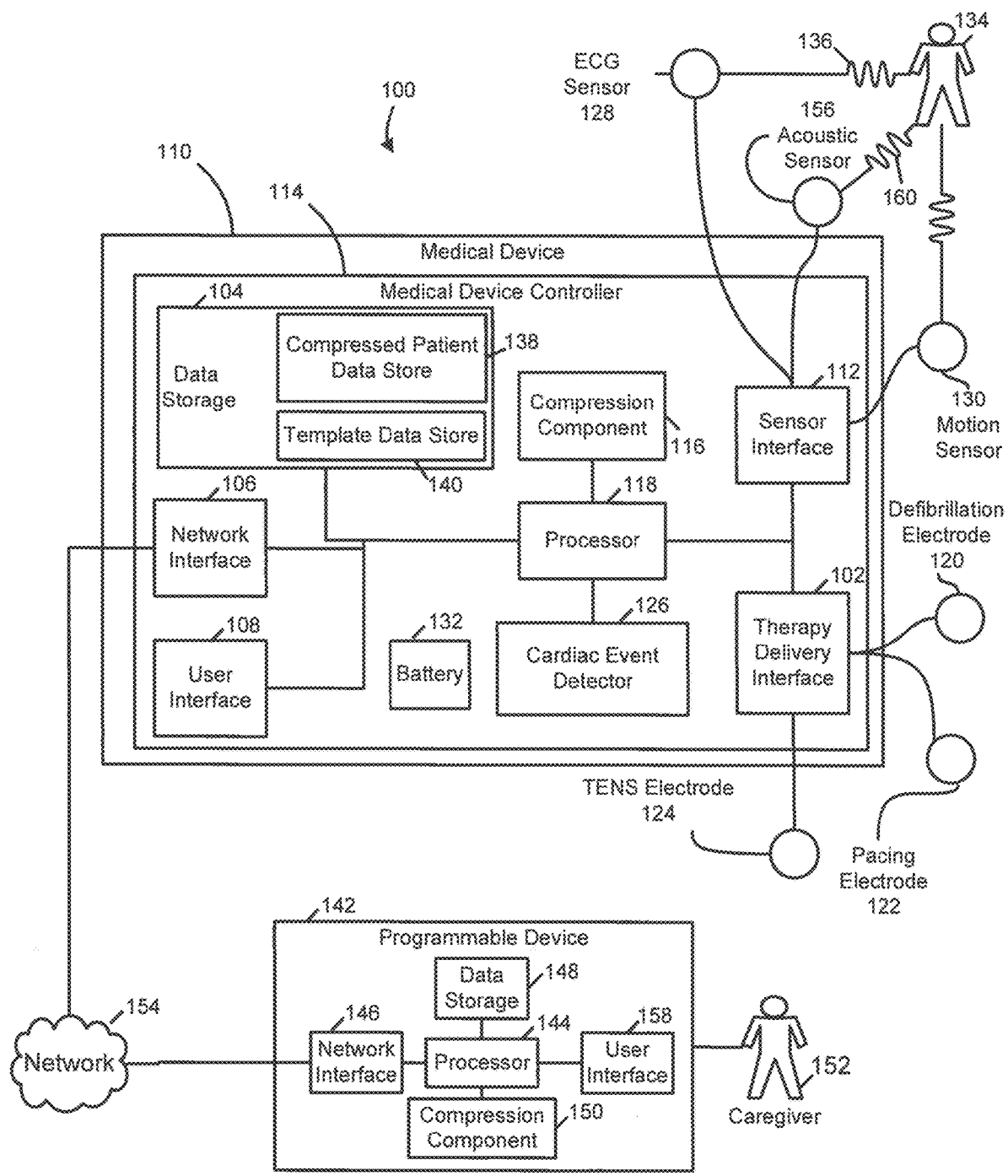
FIG. 1 is a schematic diagram of a distributed patient data compression system including a medical device and a programmable device in accordance with an example of the present disclosure.

Some aspects and examples are directed to apparatus and processes that decrease the media capacity required to transmit and/or store patient data relative to conventional techniques. Simply put, at least some of these examples encode patient data in a manner that uses fewer bits. In some examples, a medical device includes a compression component that is configured to receive patient data, encode the patient data using one or more data differencing and/or compression processes, and store and/or transmit the data to another device. In these examples, the other device, which may be a medical device or some other programmable device, receives the encoded patient data and decompresses and/or patches the patient data as needed to make the patient data useful for subsequent processing.

Examples of patient data that may be manipulated by the apparatus and processes described herein include data descriptive of patient activity, compliance, body position, pulse, body temperature, ECG signals, heart sounds, respiration, blood oxygen level, and other patient parameters. Patient data may also include patient demographic data (e.g., name, address, insurance provider, etc.), data descriptive of healthcare provider observations of the patient, and images of the patient.

Examples of the methods and systems discussed herein are not limited in application to the details of construction and the arrangement of components set forth in the following description or illustrated in the accompanying drawings. The methods and systems are capable of implementation in other examples and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, components, elements or acts of the systems and methods herein referred to in the singular may also embrace examples including a plurality, and any references in plural to any example, component, element or act herein may also embrace examples including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated references is supplementary to that of this document; for irreconcilable inconsistencies, the term usage in this document controls.

Data Compression System

FIG. 1 is a schematic diagram that illustrates the components and operation of a distributed computing system 100 when configured to compress patient data in accordance with at least one example. As shown, the distributed computing system 100 includes a medical device 110, a programmable device 142, and a communication network 154. As described further below, the medical device 110 and the programmable device 142 include specialized components configured to compress and decompress patient data. Manipulating patient data in this way enables the distributed computing system 100 to decrease the overall time required for a caregiver (e.g., the caregiver 152) to receive, evaluate, and decide upon a course of treatment for a patient (e.g. the patient 134) as compared to distributed computing systems that rely on conventional technology.

As shown in FIG. 1, the medical device 110 is associated with the patient 134 and is configured to monitor and/or treat the patient 134. The medical device 110 may include, for example, a cardiac monitoring device; any of a variety of commercially available defibrillators, such as an X Series® brand defibrillator or the LifeVest® wearable defibrillator available from ZOLL® Medical Corporation; any of a variety of commercially available ventilators, such as an EMV+™ brand ventilator available from ZOLL® Medical Corporation resuscitators, and temperature management systems. Thus the sensors used to acquire patient data may include ECG sensors (sensing electrodes), accelerometers, thermometers, pulse oximeters, and the like. Two particular examples of the medical device 110 are described further below with reference to FIGS. 2 and 3.

As illustrated in FIG. 1, the medical device 110 includes a medical device controller 114 coupled to a variety of sensors and electrodes. These sensors and electrodes may include at least one ECG sensor 128, at least one acoustic sensor 156, at least one motion sensor 130, at least one defibrillation electrode 120, at least one pacing electrode 122, and at least one transcutaneous electrical nerve stimulation (TENS) electrode 124. The sensors are coupled to the patient 134 and are configured to acquire physiologic signals 136 descriptive of parameters of the patient 134. The electrodes may be coupled to the patient 134 and are configured to provide therapy to the patient 134 as needed. In some examples, the illustrated electrodes are physically combined so that a single electrode can support multiple functions (e.g., the therapy electrodes 214 and 306 described below with reference to FIGS. 2 and 3). In addition, not all examples include all of the electrodes and sensors illustrated in FIG. 1, but rather each of these electrodes and sensors is provided to illustrate the types of sensors that may be included in particular examples.

The medical device controller 114 includes at least one processor 118, a compression component 116, a cardiac event detector 126, a sensor interface 112, a therapy delivery interface 102, data storage 104, a network interface 106, a user interface 108, and a battery 132. The data storage 104 includes a compressed patient data store 138 and a template data store 140. In some examples, these components are disposed within a single physical housing, but not every example of the medical device controller 114 includes all of these components. As such, each of the components of the medical device controller 114 is recited above is provided to illustrate the types of components that may be included in particular examples. For instance, where deployed within a medical device that monitors, but does not treat, the patient 134, the medical device controller may omit components dedicated to treatment of the patient 134 (e.g., the therapy delivery interface). Other specialized uses of the medical device controller 114 will be understood in light of this disclosure.

In specific examples, the sensor interface 112 is coupled to any one or a combination of the sensors described above and is configured to communicate with the coupled sensors to receive patient data indicative of patient parameters. As shown, the sensor interface 112 is coupled to the ECG sensor 128, the motion sensor 130, and the acoustic sensor 156. The therapy delivery interface 102 may be coupled to one or more of the electrodes described above and is configured to provide therapy to the patient 134. As shown, the therapy deliver interface 102 is coupled to one or more defibrillation electrodes 120, pacing electrodes 122, and/or TENS electrodes 124. The sensor interface 112 and the therapy delivery interface 102 may implement a variety of coupling and communication techniques for facilitating the exchange of data between the medical device controller 114, the sensors and/or the electrodes.

In some examples, the cardiac event detector 126 is configured to monitor the cardiac activity of the patient 134 to identify cardiac events experienced by the patient 134 based on physiologic signals received via, for example, the ECG sensor 128 and/or the acoustic sensor 156. This monitoring is illustrated in FIG. 1 as the patient 134 generating physiologic signals 136 (e.g., electrical and/or acoustic signals) that are acquired by the ECG sensor 128 and/or the acoustic sensor 156 and transmitted to the cardiac event detector 126 via the sensor interface 112 and the processor 118. In some examples, the cardiac event detector 126 is configured to store patient data descriptive of events identified within the physiologic signals in the data storage 104 and/or, more specifically, within the compressed patient data store 138. These events may include, for example, arrhythmias. In some examples, the cardiac event detector 126 is further configured initiate, in cooperation with other elements of the medical device controller 114, a therapeutic response to a cardiac event detected in the patient data 138. This therapeutic response may culminate in the discharge of one or more therapeutic shocks to the body of the patient 134.

In some implementations, the processor 118 includes one or more processors that each are configured to perform a series of instructions that result in manipulated data and/or control the operation of the other components of the medical device controller 114. In some implementations, when executing a specific software process as provided herein (e.g., FIGS. 4-13), the processor 118 is configured to make specific logic-based determinations based on input data received, and further capable of providing one or more outputs that can be used to control or otherwise inform subsequent processing to be carried out by the processor 118 and/or other processors or circuitry with which processor 118 is communicatively coupled. Thus, the processor 118 reacts to specific input stimulus in a specific way and generates a corresponding output based on that input stimulus. In this sense, the structure of processor 118 according to one example is defined by the flow charts shown in FIGS. 4-13. In some example cases, the processor 118 proceeds through a sequence of logical transitions in which various internal register states and/or other bit cell states internal or external to the processor 118 may be set to logic high or logic low. This specific sequence of logic transitions is determined by the state of electrical input signals to the processor 118 and a special-purpose structure is effectively assumed by the processor 118 when executing each software instruction of the software process shown in FIGS. 4-13. Specifically, those instructions anticipate the various stimuli to be received and change the implicated memory states accordingly. In this way, the processor 118 may generate and store or otherwise provide useful output signals. It is appreciated that the processor 118, during execution of a software process is capable of processing specific input signals and rendering specific output signals based on the one or more logic operations performed during execution of each software instruction. As referred to herein, the processor 118 is configured to execute a function where software is stored in a data store coupled to the processor 118 that is configured to cause the processor 118 to proceed through a sequence of various logic decisions that result in the function being executed.

In one example in accordance with FIG. 1, the data storage 104 includes and one or more of non-transitory computer readable media, such as flash memory, solid state memory, magnetic memory, optical memory, cache memory, combinations thereof, and others. The data storage 104 is configured to store executable instructions and data used for operation of the medical device controller 114 itself as well as operation of one or more of the various devices controlled by, or in communication with, the medical device controller 114.

In some examples, the user interface 108 includes one or more physical interface devices such as input devices, output devices, and combination input/output devices and a software stack configured to drive operation of the devices. These user interface elements may render visual, audio, and/or tactile content, including content relating to location-specific processing. Thus the user interface 108 may receive input or provide output, thereby enabling a user to interact with the medical device controller 114.

In some examples, the network interface 106 is coupled to the communications network 154 and is configured to exchange data with one or more devices over the network 154. For instance, in some examples in accord with FIG. 1, the network interface 106 is configured to exchange data with the programmable device 142.

In various implementations, the medical device controller 114 implements an embedded operating system that supplies file system and networking support. In one example, the medical device controller 114 includes software features that provide relational database functionality, touch screen display drivers, audio generation, BLUETOOTH wireless networking, BLUETOOTH Low Energy (BLE) Beacon technology, networking security and firewalling, and data encryption services.

The network 154 may comprise any combination of local area and/or wide area networks, using both wired and wireless communication systems. In one embodiment, the network 154 uses standard communications technologies and/or protocols. Thus, the network 154 may include links using technologies such as Ethernet, IEEE 802.11, worldwide interoperability for microwave access (WiMAX), 3G, 4G, CDMA, digital subscriber line (DSL), etc. Similarly, the networking protocols used on the network 1006 may include multiprotocol label switching (MPLS), transmission control protocol/Internet protocol (TCP/IP), User Datagram Protocol (UDP), hypertext transport protocol (HTTP), simple mail transfer protocol (SMTP) and file transfer protocol (FTP). Data exchanged over the network 1006 may be represented using technologies and/or formats including hypertext markup language (HTML) or extensible markup language (XML). In addition, all or some of links can be encrypted using conventional encryption technologies such as secure sockets layer (SSL), transport layer security (TLS), and Internet Protocol security (IPsec).

Compression Components

The patient data compression system 100 illustrated in FIG. 1 includes several components that, in combination, implement differencing, compression, decompression, and patching of patient data. These components are described further below.

In some examples, the compression component 116 is executable by the at least one processor 118 and is configured to execute any of a variety of data differencing and/or compression processes, such as any of the data differencing and compression processes described further below with reference to FIGS. 4-13. Some of these processes act upon data stored in a conventional format. Others of these processes generate difference data, e.g., data that is descriptive of differences between a physiologic signal acquired from the patient 134 and a corresponding template associated with the patient 134, and act upon this data. In other examples, difference data may comprise data that is descriptive of one or more differences between different samples of physiologic signals of the patient, for example samples acquired at different times (e.g. sequentially, at different time points, etc.) or from different sources (e.g. from different sensors, pairs of electrodes positioned at different parts of the body, etc.). Some examples of the compression component 116 are configured to act upon difference data to increase the effectiveness of compression processes. As shown in FIG. 1, the compression component 116 is configured to store the templates used to generate difference data in the template data store 140. The compression component 116 is also configured to store compressed patient data, in conventional or differenced form, in the compressed patient data store 138.

Is some examples, the compression component 116 is also configured to use difference data to reconstruct patient data descriptive of a physiologic signal from a corresponding template. This reconstruction process may be referred to as patching and is described further below with reference to FIGS. 4-13.

In some examples, the compression component 116 is configurable to operate in a template mode and/or a compression mode. When operating in the template mode, the compression component 116 records physiologic signals 136 of the patient 134 and generates one or more templates based on the recorded signals. One example of acts the compression component 116 is configured to execute when operating in template mode is described further below with reference to FIG. 4. When operating in compression mode, the compression component 116 calculates difference data and/or compresses patient data. Examples of acts the compression component 116 is configured to execute when operating in compression mode are described further below with reference to FIGS. 4-13.

Additionally, in some examples, the compression component 116 includes a shielding component that is configured in accordance with the shielding component disclosed in U.S. Patent Application Publication No. 2016/0321418, titled CUSTOMER- OR PATIENT-BASED SELECTIVE DATA ENCRYPTION IN MEDICAL DEVICE MANAGEMENT, published Nov. 3, 2016, which is hereby incorporated herein by reference in its entirety. In some examples, the shielding component increases the security of the compressed data by selectively shielding data portions of the compressed data.

In some examples, the compression component 116 is configured to transmit differenced and/or compressed data to another device (e.g., the programmable device 142) via the network interface 106 and the network 154. The programmable device 142 includes a network interface 146, a processor 144, a compressed patient data store 148, and a compression component 150. The programmable device 142 is associated with and configured to be operated by the caregiver 152. For example, the caregiver 152 may use the programmable device 142 to review current patient data (e.g., pulse, heart sounds, height, weight, caregiver notes on the condition of the patient 134) and well as historical patient health data (e.g., trends as a function of time of pulse, blood pressure, heart rhythm).

The programmable device 142 can include various computing devices that can be placed in communication with the network 154. In some examples, the programmable device 142 is a computing device capable of receiving user input as well as transmitting and/or receiving data via the network 154. In one embodiment, the programmable device 142 is a computer system, such as a desktop or laptop computer. In another embodiment, the programmable device 142 is a device having computer functionality, such as a personal digital assistant (PDA), mobile telephone, tablet computer, smartphone or similar device.

The network interface 146, processor 144, data storage 148, compression component 150, and user interface 158 of the programmable device 142 are analogous to those described above in the context of the medical device controller 114 and need no further explanation.

Example Ambulatory Medical Device

In some examples, the medical device 110 described above with reference to FIG. 1 is an ambulatory medical device, e.g., a wearable medical device. For example, such an ambulatory medical device is capable of substantially continuous use by the patient. That is, the ambulatory medical device may be continuously used, except for sporadic periods during which the use temporarily ceases (e.g., while the patient bathes, while the patient is refit with a new and/or a different garment, while the battery is charged/changed, while the garment is laundered, etc.). For example, such substantially continuous use as described herein may nonetheless qualify as continuous use.

Figure 2:
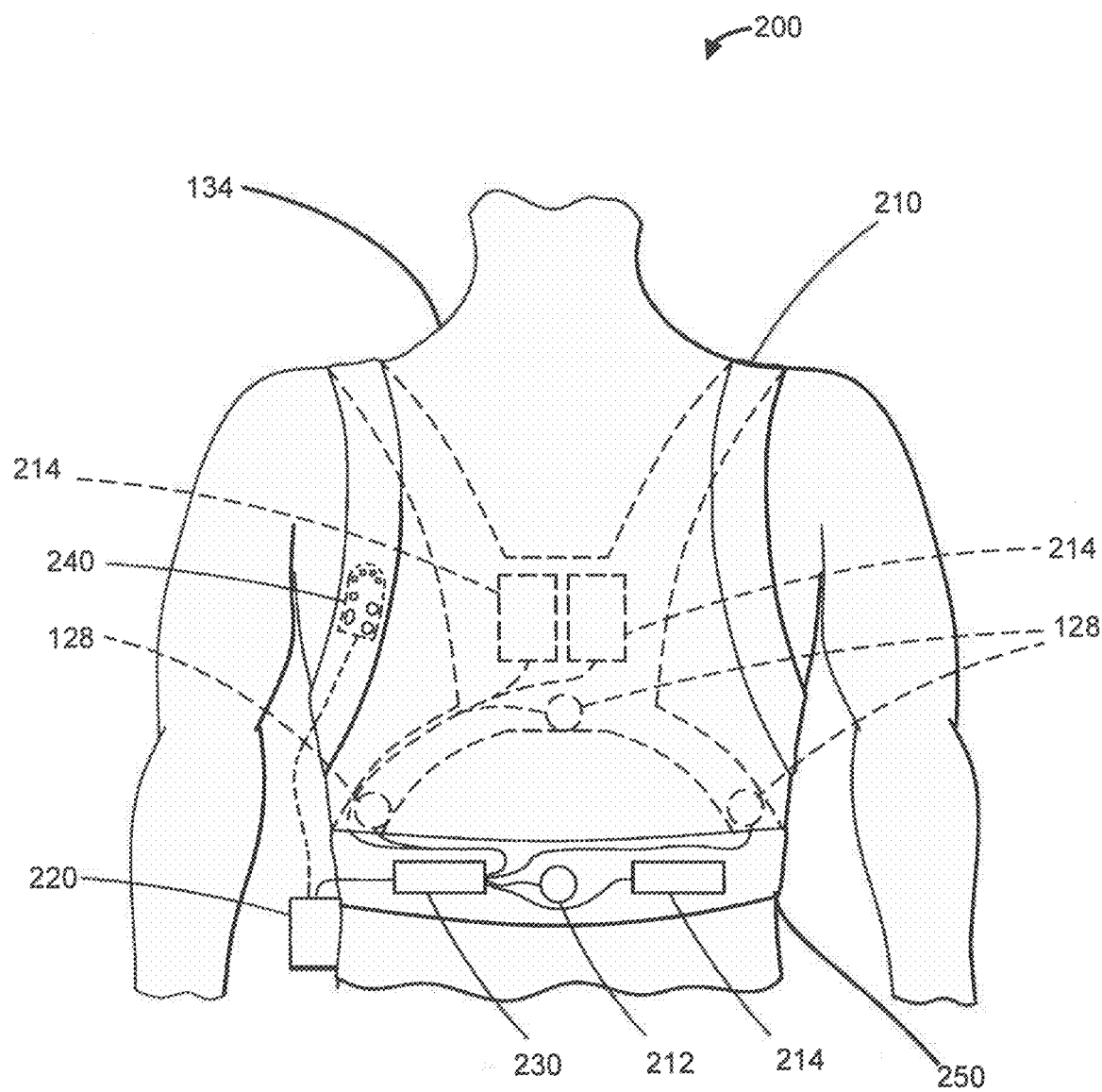
FIG. 2 is a schematic diagram of an ambulatory medical device in accordance with an example of the present disclosure.

Further, such an ambulatory medical device may also be configured for use for an extended period of time. For example, the ambulatory medical device can be configured to be used by the patient for hours, days, weeks, months, or even years. In some implementations, the extended use may be substantially continuous in nature. The use of the ambulatory medical device can include continuous wear by the patient, attachment to the patient, and/or monitoring of the patient. The ambulatory medical device may carry out its monitoring in periodic or aperiodic time intervals or times. For example, the monitoring during intervals or times can be triggered by a user action or another event. For example, one or more durations between the periodic or aperiodic intervals or times can be user-configurable, FIG. 2 illustrates an ambulatory medical device 200 that is controlled by, or otherwise in communication with, the medical device controller 114. The ambulatory medical device 200 is worn by the patient 134 and includes sensors that monitor the physiology of the patient 134 over, in some instances, an extended time period (e.g., days, weeks, or even months). The ambulatory medical device 200 may also include treatment components, such as treatment electrodes, that are configured to treat the patient when warranted. Particular examples of the ambulatory medical device 200 include, among other devices, mobile cardiac telemetry devices and/or wearable defibrillators, such as the LifeVest® brand wearable defibrillator available from ZOLL® Medical Corporation of Chelmsford, MA.

As shown, the medical device 200 includes a garment 210, a plurality of ECG sensors 212, a plurality of therapy electrodes 214, a medical device controller 220, a connection pod 230, a patient interface pod 240, and a belt 250. The medical device controller 220 may incorporate the medical device controller 114. The plurality of ECG sensors 212 can be disposed at various positions about the patient's body. As shown, the ECG sensors 212 are electrically coupled to the medical device controller 220 through the connection pod 230. In some implementations, some of the components of the wearable medical device 200 are affixed to the garment 210 that can be worn on the patient's torso. For example, as shown in FIG. 2, the controller 220, at least some of the ECG sensors 212, and, optionally, one or more therapy electrodes 214 can be mounted on a belt 250 worn by the patient. The ECG sensors 212 and the connection pod 230 can be assembled or integrated into the garment 210 as shown. The ECG sensors 212 are configured to monitor the cardiac function of the patient (e.g., by monitoring one or more cardiac signals of the patient). The plurality of therapy electrodes 214 can be electrically coupled to the controller 220 through the connection pod 230. The therapy electrodes 214 are configured to deliver one or more therapeutic defibrillating shocks to the body of the patient if the medical device controller 220 determines that such treatment is warranted. The connection pod 230 may include electronic circuitry and one or more sensors (e.g., a motion sensor, an accelerometer, etc.) that are configured to monitor patient activity.

The wearable medical device 200 may include the optional patient interface pod 240 that is coupled to the medical device controller 220. For example, the patient interface pod 240 may include patient interface elements such as a speaker, a microphone responsive to patient input, a display, an interactive touch screen responsive to patient input, and/or physical buttons for input. In some implementations, these elements are incorporated into a housing of the controller 220. The patient interface pod 240 may be wirelessly coupled with the controller 220. The patient interface pod 240 may take other forms and include additional functionality. For instance, the patient interface pod 240 may be implemented on a smartphone, tablet, or other mobile device carried by the patient. In another example, the patient interface pod 240 may be worn as a watch about the wrist of the patient, or as a band about an upper arm of the patient. In some implementations, the controller 220 may communicate certain alerts and information and/or be responsive to patient input via both the patient interface elements included in the controller 220 and the patient interface pod 240. The patient and/or caregiver can interact with a touch display or the patient interface pod 240 to control the medical device 200.

Example Automated Medical Device

Figure 3:
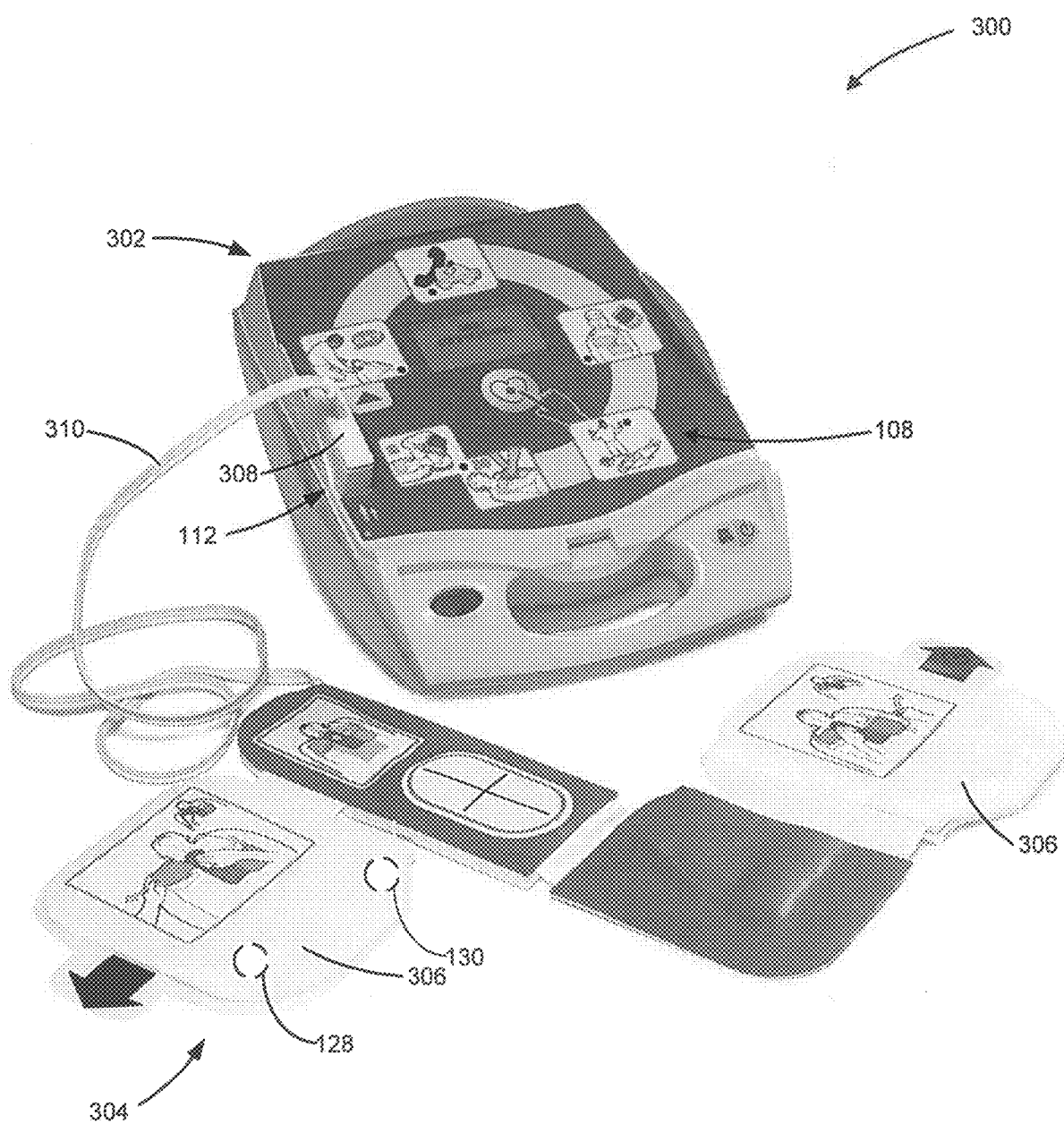
FIG. 3 is a schematic diagram of another medical device in accordance with an example of the present disclosure.

In some examples, the medical device 110 described above with reference to FIG. 1 is an automated external defibrillator (AED) An example AED 300 is illustrated in FIG. 3 AEDs are small portable defibrillators that are capable of monitoring cardiac rhythms, determining when a defibrillating shock is necessary, and administering the defibrillating shock either automatically, or under the control of a trained rescuer (e.g., an EMT or other medically training personnel). The AED 300, in addition, may be configured to provide counseling to an operator as to how to perform cardiac resuscitation (CPR).

The AED 300 illustrated in FIG. 3 may be, for example, an AED Plus® automated external defibrillator available from ZOLL® Medical Corporation. As shown, the AED 300 includes, or is in communication with, a medical device controller (e.g., medical device controller 114) which may be incorporated into a housing 302. The AED 300 may further include an electrode assembly 304. The electrode assembly 304 includes one or more ECG sensors 128, one or more motion sensors 130, one or more therapy electrodes 306 housed within defibrillation pads, a connector 308, and wiring 310. The wiring 310 electrically couples the connector 308 to the one or more ECG sensors 128, the one or more motion sensors 130, and the one or more therapy electrodes 306. As shown in FIG. 3, the connector 308 is configured to couple the electrode assembly 304 to the AED controller and, more specifically, the one or more ECG sensors 128 and the one or more motion sensors 130 to the sensor interface 112 and the one or more therapy electrodes 306 to the therapy delivery interface 102.

The AED 300 is configured to detect the cardiac rhythm of the subject using ECG and heart sounds data and provide pacing and defibrillating shocks to the subject as appropriate. This process is similar to the process described with regard to a medical device controller (such as the medical device controller 220) of the ambulatory medical device 200. The user interface 108 of the AED 300 may include a variety of components configured to communicate with the operator including, but not limited to, a display screen, a speaker, and one or more buttons. In this example, the AED 300 includes a display screen to display notifications to an operator. The notifications may provide instructions to the operator regarding the proper administration of CPR to the subject. The notifications on the display may be accompanied by audible alerts from the speaker to further assist the operator in administering CPR to the patient.

Example Compression Processes

As described above, in some examples a medical device (e.g., the medical devices 110, 200, and 300) include a compression component (e.g. the compression component 116) configured to execute data differencing and/or compression processes that make space and time efficient use of media used to store and/or transmit patient data. Use of the compression component may reduce patient data transmission and/or reception latencies, especially where the patient data is exchanged via low bandwidth connections. Example techniques and their corresponding processes as implemented by various examples of the compression component are described further below. Also described below are processes that the same or another compression component (e.g., the compression component 150) may be configured to execute to decompress and/or patch patient data to render the patient data usable by subsequent processes.

Template Switching

Figure 4:
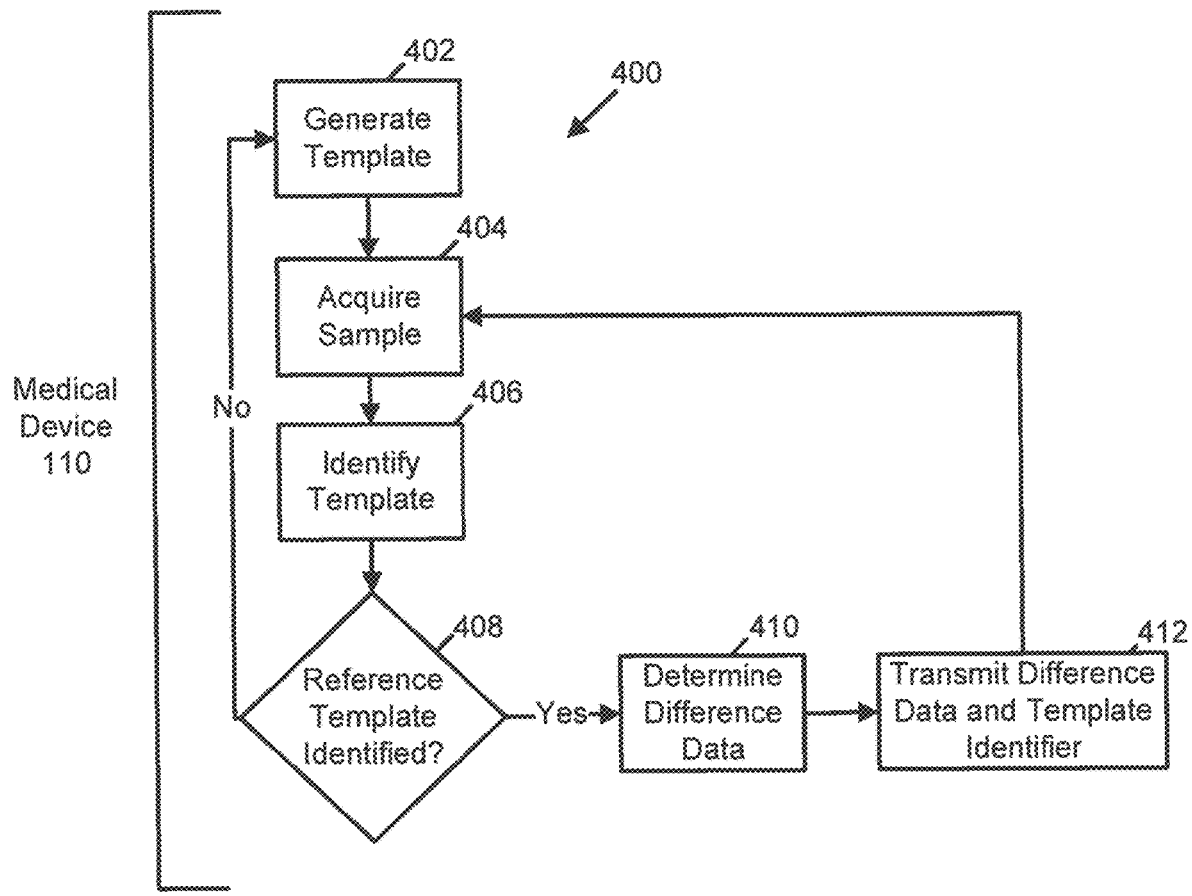
FIG. 4 is a flow diagram illustrating a data differencing and compression process in accordance with an example of the present disclosure.

In some examples, the compression component 116 is configured to execute a multi-template data differencing process, such as the data differencing process 400 illustrated in FIG. 4. When executing according to this configuration, the compression component 116 leverages two or more templates (e.g., from the template data store 140) to advantageous effect by monitoring the similarity of a reference template to acquired samples and by changing the reference template where the similarity fails to meet one or more criterion. To decrease the volume of difference data, some examples of the compression component 116 record one or more templates specific to an individual patient (e.g., the patient 134) prior to differencing the patient's data. These templates may correspond to various levels of patient activity (e.g., at rest, conducting daily activities, exercising, etc.) so that each level of activity the patient may experience while being monitored by the medical device has a corresponding, prerecorded template. Where the patient data sample is ECG data, these templates may be recorded during, and therefore represent, a patient's cardiac cycle at various patient activity levels (e.g., at rest, conducting daily activities, exercising, etc.).

FIG. 4 illustrates one example of a multi-template data differencing process 400. The data differencing process 400 starts in the act 402 with the compression component 116 generating one or more templates. The act 402 may be executed when the compression component 116 is configured to operate in a template mode. In some examples, the act 402 is executed prior to clinical use of the medical device by the patient. For example, where the medical device is a wearable medical device, there may be fitting procedure prior to deployment of the medical device to the patient.

During this fitting procedure, one or more segments of physiologic data may be collected from the patient. The physiologic data may include ECG, heart sounds, breath sounds, peripheral capillary oxygen saturation (SpO2), etc. The duration of the segments may be 5-10 seconds, or longer, e.g. 1, 2, 3, 5, 10 minutes. Multiple segments may be collected with the patient under varying degrees of physiologic stress. For instance, the patient may undergo an ECG stress test, whereby they walk or jog on a treadmill for a specified period, and the heart rates are brought from normal rates up to near the patient's limit of endurance. Multiple templates may then be created for the varying heart rates: resting rate, maximum rate, and then in some examples multiple rates in between, e.g. 1.1 times resting rate, 1.2 times resting rate, 1.3 times resting rate, 1.4 times resting rate, etc. up to 0.9 times maximum rate.

In other examples, the act 402 is executed after clinical use has started, but prior to any data differencing being performed by the compression component 116. In these examples, during the initial 1-2 minutes, 10 minutes, 1 hour, or other initial time period, the ECG or other physiologic data is acquired from the patient and stored. Then one or more templates is created for later use in data differencing and compression.

In some examples of the act 402, the compression component 116 creates templates by creating median beats. For example, a median beat may be created from one or more leads, e.g. up to 12 leads of the ECG. Median beats are utilized to minimize the impact of noise present in any given single beat. Multiple global measurements can be determined utilizing the median beats including the PR, QRS and QT duration. Median beat formation involves the identification of a "primary" beat type within a sequence of beats. This categorization identifies beats which are to be included in the median or representative beat formation. Beats which are not considered part of the "primary" class are not included in the formation of the median. In applying these criteria, beats such as occasional premature ventricular complexes can be excluded from the median beat formation. Following selection of beats, the beats can be aligned and the median beat is identified. In general, automated measurements come from a representative beat based on 3 or more seconds of the digitally-acquired ECG. Typical data rates can be in the range of 100-1000 Hz with resolution in the range of 0.5-1 microvolt per least significant bit (LSB) and 16-24 bits of dynamic range. The process begins by taking one or more leads of the ECG and creating a median complex from a primary, or dominant, normal beat. All of the beats with the primary morphology can be used for the creation of the median beat.

After medians are created for each lead, a global median can be created by aligning the individual median beat. From there, the earliest onset to the latest offset can be measured for all variables (PR, QRS and QT). In many cases, the result of using the earliest onset to the latest offset will be to have a longer QT interval measurement than the human reading. Heart rates for automated algorithms can be calculated over the entire 10-second ECG. Alternative template creation techniques may be used. One such alternative, segmented beat modulation, is described by Agostinelli, et al ("Extracting a clean ECG from a noisy recording: A new method based on segmented-beat modulation", Computing in Cardiology Conference (CinC, 2014, ISSN: 2325-8861).

Templates generated in the act 402 may represent a signal within various domains. These domains include the time domain, the frequency domain, and the wavelet domain. Templates that represent a signal within the time domain include data fields configured to store values that represent the amplitude and timing of each signal acquired by the medical device. Templates that represent a signal within the frequency domain include data fields configured to store values that represent Fourier coefficients as may be generated by applying a Fourier transform to each signal acquired by the medical device. Templates that represent a signal within the wavelet domain include data fields configured to store data specifying a wavelet prototype function and values that represent wavelet coefficients as may be generated by applying a wavelet transform to each signal acquired by the medical device. Other templates that represent signals in other domains may be used without departing from the scope of the examples disclosed herein. For examples where the compression engine is configured to store values of transform function coefficients in the templates, the compression engine may be configured to store only a subset of the coefficients that are the most informative (e.g., a predefined number of largest coefficients, non-zero coefficients, etc.).

In act 404, the compression component 116 receives a sample of physiologic data (e.g., the sample 136) generated by the patient and acquired by the medical device. The one or more sensors used to acquire the physiologic data sample may include ECG sensors, accelerometers, thermometers, pulse oximeters, and the like. For instance, in some examples, the physiologic data sample is an ECG sample collected from a 12 lead sensor arrangement for one complete cardiac cycle.

In act 406, the compression component 116 attempts to identify a template that matches the physiologic data sample to a predefined degree. For instance, in one example of the act 406, the compression component 116 calculates measures of similarity between each template stored in the template data store 140 and the physiologic data sample (transformed, if needed, into the domain of each template). These measures of similarity may be, for example, correlation coefficients resulting from calculations of cross-correlations between the physiologic data sample and each template. In some examples, the compression component 116 compares the measures of similarity to one another and a minimum threshold. In these examples, the compression component 116 identifies a template associated with the highest correlation coefficient and, where that correlation coefficient is greater than the minimum threshold, selects the template as a reference template for the physiologic data sample. Because there are a variety of templates stored in the template data store 140 corresponding to a variety of the patient's physiologic states across a range of patient activity levels, the compression component 116 can select, in many cases, a reference template that closely matches the exact waveform morphology of the physiologic data sample. The compression component 116 can make this selection at multiple points during the course of the patient's day or over an extended period, during periods of both rest as well as varying levels of physical activity.

In act 408, the compression component 116 determines whether a reference template was identified in the act 406. If not, and no arrhythmia has been detected by the medical device (e.g. via execution of the cardiac event detector 126), the compression engine executes the act 402 with the physiologic data sample to generate and/or modify a template to correspond to the physiologic data sample. If a reference template was identified in the act 408, the compression component 116 executes act 410.

In the act 410, the compression component 116 determines difference data that represents differences between the reference template and the physiologic data sample. In act 412, the compression component 116 locally stores, in the compressed patient data store 138, and/or transmits the difference data and a reference template identifier, where there was a change in the reference template, to the compression component 150. In some examples, the compression component 116 compresses the difference data (and the reference template identifier, where present) using conventional compression techniques prior to storage and/or transmission. After completing the act 412, the compression component 116 returns to the act 404 to acquire the next physiologic data sample.

Figure 5:
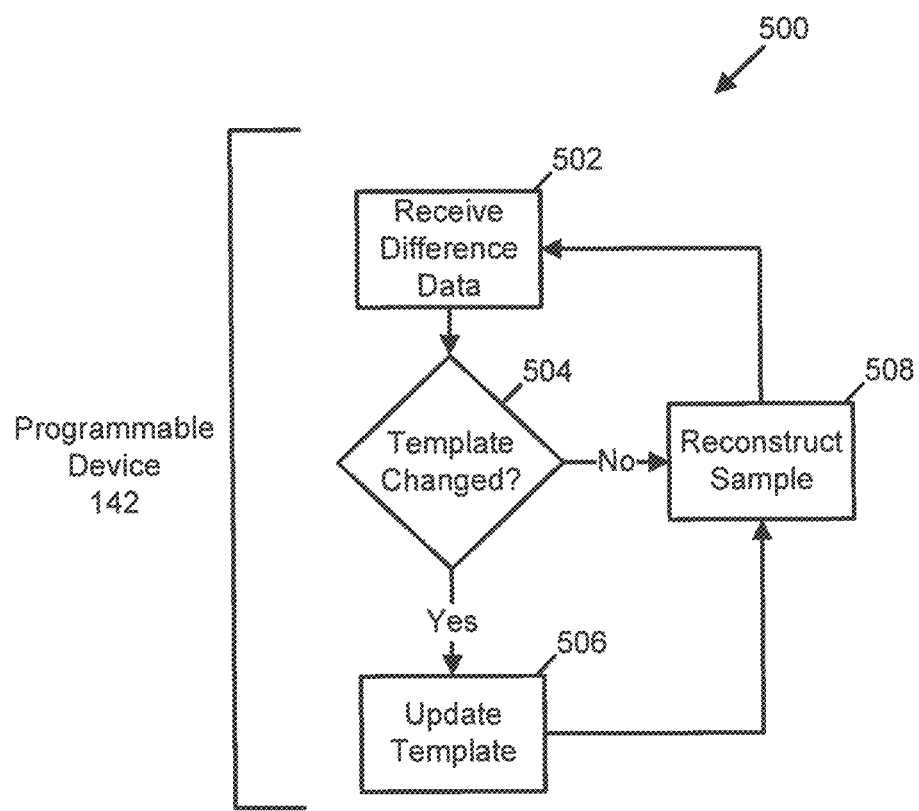
FIG. 5 is a flow diagram illustrating a decompression and data patching process in accordance with an example of the present disclosure.

FIG. 5 illustrates a corresponding patching process 500 executed by a compression component 150 to reconstruct the physiologic data sample acquired by the medical device during execution of the data differencing process 400. As shown, the patching process 500 starts in act 502 where a programmable device (e.g., the programmable device 142) receives the difference data. In act 504, the programmable device parses the difference data to determine whether the reference template changed. If so, the programmable device updates the reference template in act 506. Otherwise, the programmable device proceeds directly to act 508 and reconstructs the sample using a local stored reference template and the difference data. After completing the act 508, the programmable device returns to the act 502 and receives a next set of difference data.

Selective Communication

In some examples, compression components 116 and 150 decrease the latency time between acquisition of physiologic signals from the patient and receipt of patient data at a remote caregiver (e.g., the caregiver 152) when transmitting over a bandwidth limited channel by selectively storing, transmitting, and/or receiving high resolution data based on feedback received regarding low resolution data. As used herein "resolution" may refer, in addition to its ordinary meaning, to resolution in the time domain or amplitude. Higher resolution when, characterizing the instantaneous signal amplitude of the particular waveform, could be conveyed by a smaller-sized (and therefore more sensitive) LSB and larger sample word size (to keep the dynamic range the same while having a smaller LSB). Alternatively or additionally, higher resolution can be recorded by faster sampling rates to get a higher resolution reproduction of the signal in time. This high resolution data may include data that is recorded at high data rates or smaller LSB and for which conventional latency times are long (e.g., ECG data). The low resolution data may include data that is recorded at low rates, data that summarizes high resolution data, and/or data for which conventional latency times are short. By utilizing feedback received regarding the low resolution data, compression components in accordance with these examples avoid transmitting some or most of the high resolution data, thereby utilizing less bandwidth than conventional techniques that transmit all or most of the high resolution data.

Figure 6:
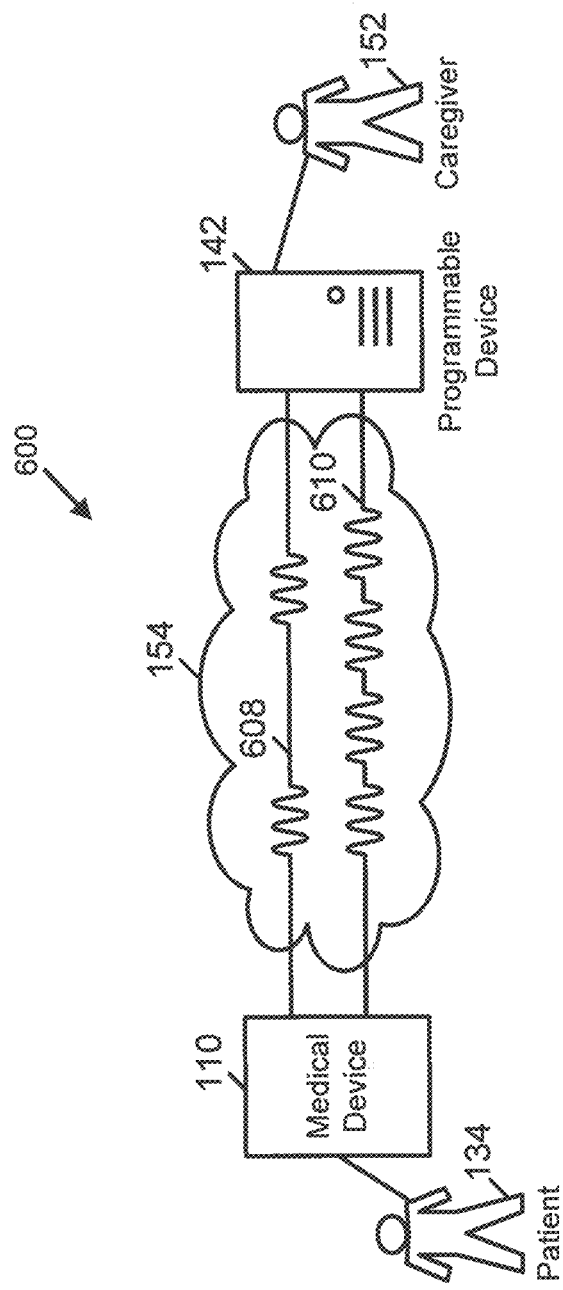
FIG. 6 is a schematic diagram illustrating a selective transmission arrangement in accordance with an example of the present disclosure.

FIG. 6 illustrates a system 600 that selectively processes high resolution data in accordance with at least one example. As shown, FIG. 6 depicts a medical device 110 connected to the programmable device 142 via a network 154. The medical device 110 is associated with the patient 134 and transmits at least two data streams 608 and 610 of different resolutions of the same patient data to the programmable device 142 via the network 154. In some examples, the at least two data streams 608 and 610 may be transmitted over the same communications channel (e.g. a cellular "4G" wireless phone channel) or alternatively, the two or more data streams may be transmitted over separate channels (e.g. two separate phone calls to the same location made by the same transmitting cellphone).

In this example, the data stream 608 includes low resolution data, and the data stream 610 includes high resolution data. In some examples, low resolution data transmitted via the data stream 608 is a lossy compressed version of the high resolution data to facilitate transmission speed. In these examples, the high resolution data 610 is compressed using a typically lossless, or at least high fidelity, compression process to increase accuracy but at the cost of delayed transmission.

In some examples, the compression component 116 transmits high resolution data and low resolution data simultaneously. However, unlike a standard dual data stream transmission with a single transmission buffer, in these examples the compression component 116 prioritizes low resolution data over high resolution data. In some examples, this prioritization is not dependent on the amount of high resolution data that is available to be transmitted. Rather, in these examples, the compression component 116 implements two distinct buffers, one for high resolution data and one for low resolution data. Further, in these examples, the compression component 116 maintains priority with the low resolution buffer until the low resolution buffer is empty or contains only data placed in the buffer recently enough to fall within an acceptable latency period. The acceptable latency period may be specified by a configurable parameter of the compression component 116. Example durations of acceptable latency periods include 10 milliseconds, 100 milliseconds, 500 milliseconds, 1 second, 5 seconds, and 10 seconds. In some examples, at the receiving side, the compression component 150 of the programmable device 142 may parse and display (via the user interface 108) information based on the high resolution data and information based on the low resolution data as both are received. In some examples, the compression component 150 implements a high resolution buffer and a low resolution buffer. The compression component 150 may prioritize the low resolution buffer over the high resolution buffer using the same methodology as the compression component 116.

It is appreciated that this data stream prioritization scheme is not limited to two levels of resolution. Other examples of the compression components 116 and 150 may implement one or more intermediate levels of resolution in addition to the high resolution data stream 610 and the low resolution data stream 608.

As shown in FIG. 6, the programmable device 142 is associated with the caregiver 152 and presents information based on both data streams 608 and 610 to the caregiver 152. As described further below, the caregiver 152 can provide, to the medical device 110, feedback that indicates portions of the high resolution data that are of interest. This feedback enables the compression component 116 to skip over any high resolution data in the high resolution buffer that is not of interest and to queue for transmission only the high resolution data that is of interest, thereby avoiding transmission of un-transmitted high resolution data in the buffer that is not of interest. In such a case, the latencies can be re-calculated by the compression component 116 and displayed appropriately by the compression component 150 via the user interface 158 of the programmable device 142. The feedback that indicates the portions of interest may be input by the caregiver 152 via a touch-screen interface of the user interface 158, where, for instance, the caregiver 152 may draw a box or other visual selection around the waveform portion of interest.

Figure 7:
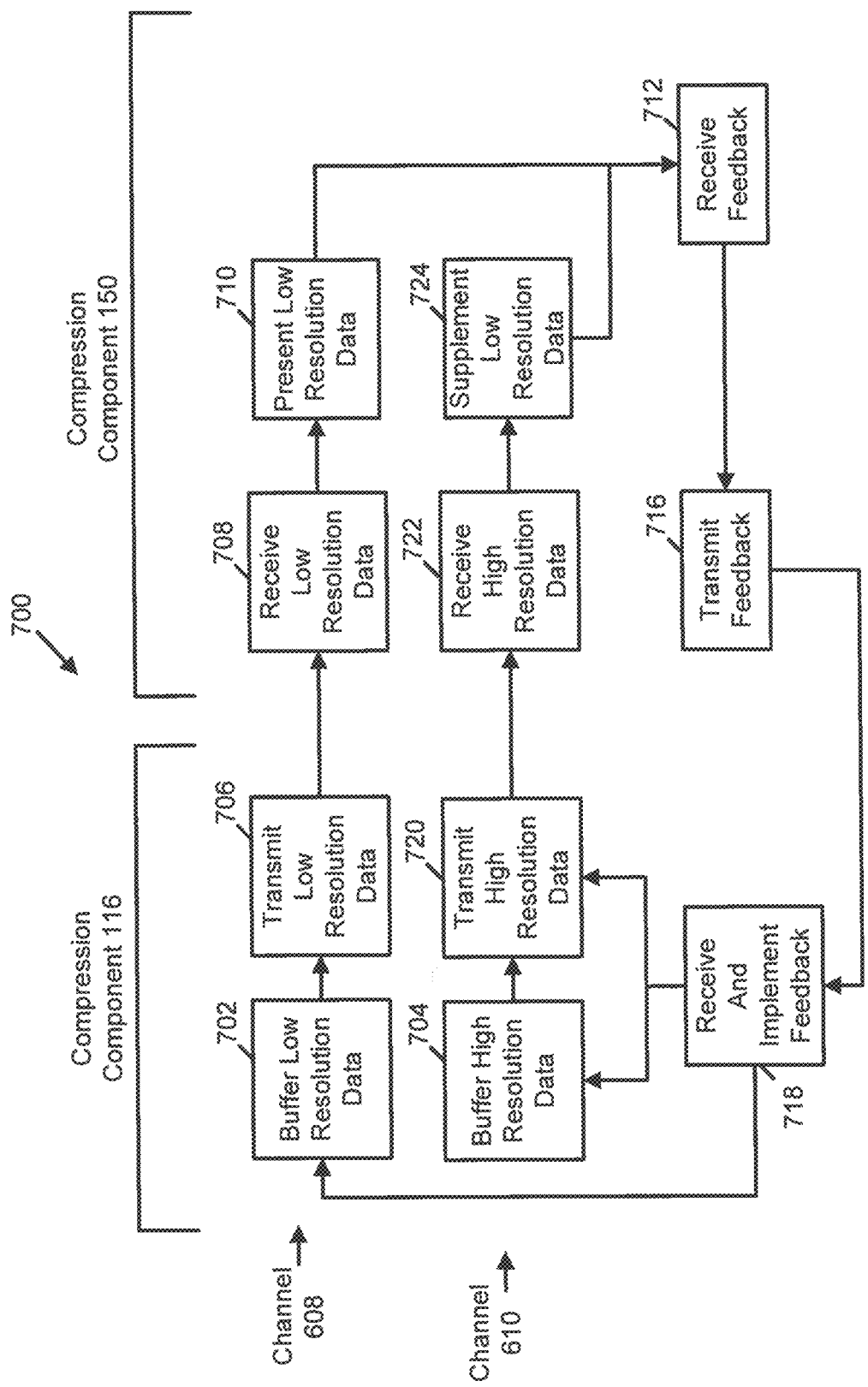
FIG. 7 is a flow diagram illustrating a selective transmission process in accordance with an example of the present disclosure.

FIG. 7 illustrates a selective transmission process 700 executed by the system 600 in accordance with at least one example. As shown, the transmission process 700 starts in act 702 with the compression component 116 buffering low resolution data into a first data structure configured to store low resolution data. In act 704, the compression component 116 buffers high resolution data into a second data structure configured to store high resolution data. In some examples, the first data structure and the second data structure are the same data structure (e.g., a transmission buffer). In other examples, the first data structure and the second data structure are distinct data structures (e.g., distinct transmission buffers).

In act 706, the compression component 116 transmits low resolution data to the compression component 150 via the data stream 608. In act 708, the compression component 150 receives the low resolution data via the data stream 608. In act 710, the compression component 150 presents the low resolution data to the caregiver 152 via the user interface 158. In act 712, the compression component 150 receives feedback from the caregiver 152 identifying one or more portions of the low resolution data that are of interest. In act 716, the compression component 150 transmits the feedback to the compression component 116. In act 718, the compression component 116 receives the feedback and implements the feedback. In one example, the compression component 116 implements the feedback by queuing the high resolution data of interest (as identified in the feedback) for transmission and executing the acts 720 and 702. By queuing the high resolution data of interest, the compression component 116 skips any high resolution data in the second data structure that is not of interest. In the act 720, the compression component 116 transmits the high resolution data that is queued for transmission to the compression component 150 via the data stream 610. In act 722, the compression component 150 receives the high resolution data via the data stream 610. In the act 724, the compression component 150 supplements the presentation of the low resolution data with the high resolution data and the feedback loop repeats.

As described above, in some examples, the high resolution data is buffered into the first data structure but is not transmitted until feedback is received. Also, as described above, the compression component 116 may allocate and load a single data structure (e.g., a transmit buffer) with both high resolution data and low resolution data, but in some examples, the compression component 116 allocates and loads two separate data structures, one for each resolution of data. In examples where the high resolution data is sent only after feedback regarding the low resolution data is received and processed, the second data structure may store a pre-specified duration of high resolution data. In these examples, the compression component 116 starts transmitting select portions of high resolution data buffered in the second data structure, or all of the high resolution data buffered in the second data structure, in response to receiving the feedback regarding the low resolution data.

In some examples, no feedback from the compression component 150 is required; both resolutions of data are transmitted simultaneously, and the caregiver 152 merely waits for the latency period to pass in order to review the presentation of the high resolution data.

The processes disclosed herein each depict one particular sequence of acts in a particular example. The acts included in these processes may be performed by, or using, one or more programmable devices specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

Recursive Processing

Figure 8:
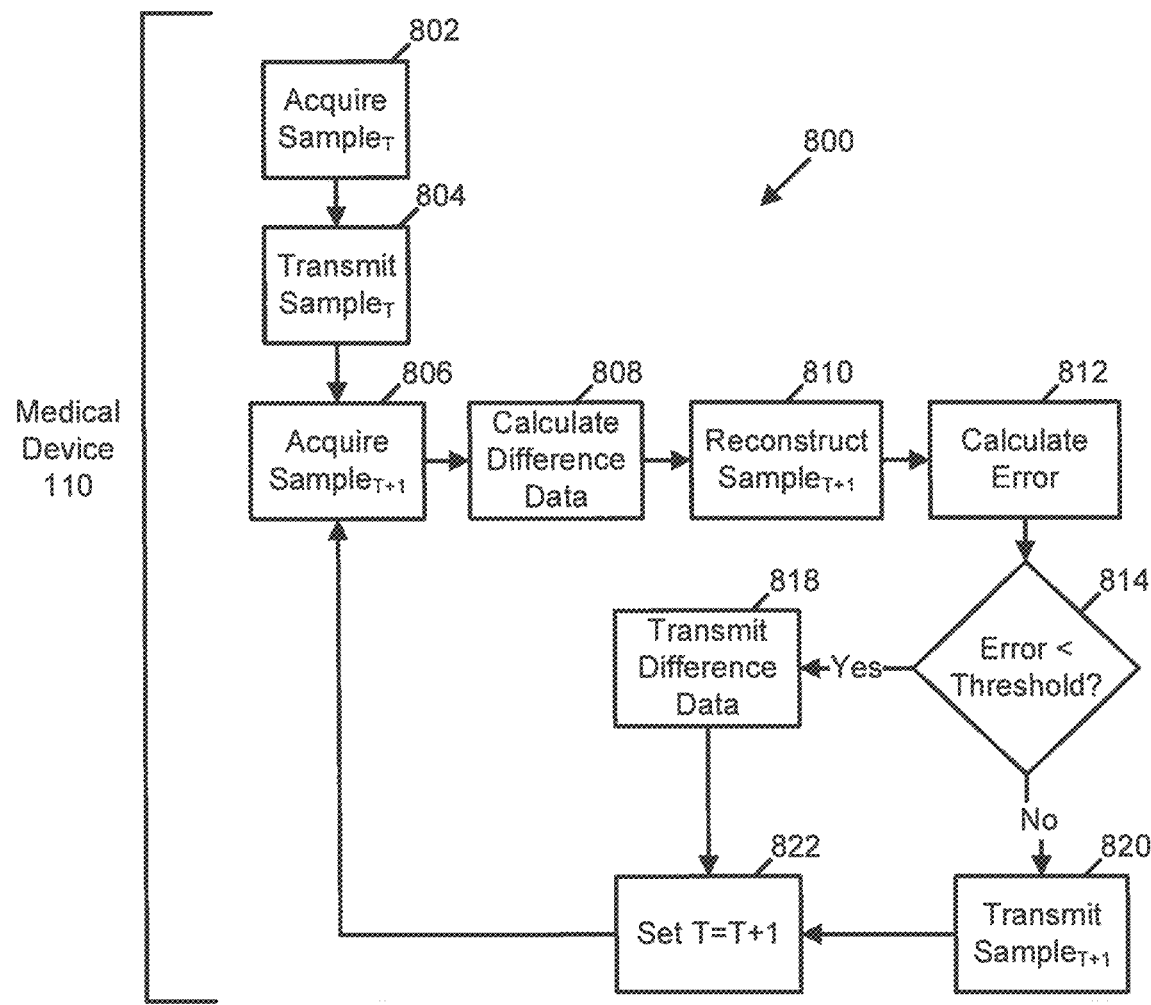
FIG. 8 is a flow diagram illustrating a recursive data differencing and compression process in accordance with an example of the present disclosure.

In some examples, the compression component 119 is configured to decrease the computing resources required to store and/or transmit patient data by executing a data differencing process configured to identify and transmit differences between sequential samples of physiologic signals of the patient rather than full copies of each sample. FIG. 8 illustrates a data differencing process 800 in accordance with these examples. As shown, the differencing process 800 starts in the act 802 with the compression component 119 receiving data descriptive of an acquired sample$_t$ of a physiologic signal of the patient. This physiological signal may include, for example, an ECG signal. In act 804, the compression component 119 transmits the sample$_t$ to the compression component 150. In act 806, the compression component 119 receives data descriptive of another acquired sample$_{t+1}$ of the physiologic signal of the patient.

In act 808, the compression component 116 calculates difference data descriptive of a difference between the sample$_t$ and the sample$_{t+1}$. In some examples, calculating this difference data may include aligning the phase of the sample$_{t+1}$ to the phase of the sample$_t$ and subtracting data values of the sample$_t$ (e.g., representative of amplitude) from corresponding data values of the sample$_{t+1}$.

In act 810, the compression component 116 reconstructs the sample$_{t+1}$ from the difference data and sample$_t$. In some examples, reconstructing the sample$_{t+1}$ from the difference data and sample$_t$, includes adding the difference data to the data values of sample$_t$ and shifting the phase of the sum to the phase of the sample$_{t+1}$. In act 812, the compression component 116 calculates an amount of error in the reconstructed sample$_{t+1}$ by calculating a difference (e.g., cross correlation) between the sample$_{t+1}$ and the reconstructed sample$_{t+1}$. In one example, the amount of error calculated in the act 812 is the magnitude by which the cross correlation coefficient, when normalized to the range of [−1, 1], deviates from 1. In a more general sense, the amount of error may be any metric that indicates the degree of fit between the sample$_{t+1}$ and the reconstructed sample$_{t+1}$.

In act 814, the compression component 116 determines whether the calculated error exceeds a threshold. If so, the compression component 116 transmits sample$_{t+1}$ to the compression component 150 in act 820. Otherwise, the compression component 116 compresses (e.g., via Huffman encoding), stores, and/or transmits the compressed difference data to the compression component 150 in act 818. In act 822, the compression component 116 replaces sampler with sample$_{t+1}$ and returns to the act 806 to acquire the next sample of the physiologic signal of the patient (a new sample$_{t+1}$).

In some examples, the error checking acts 810, 812, and 814 are unnecessary and omitted, and the data differencing process 800 proceeds directly from the act 808 to the act 818.

Figure 9:
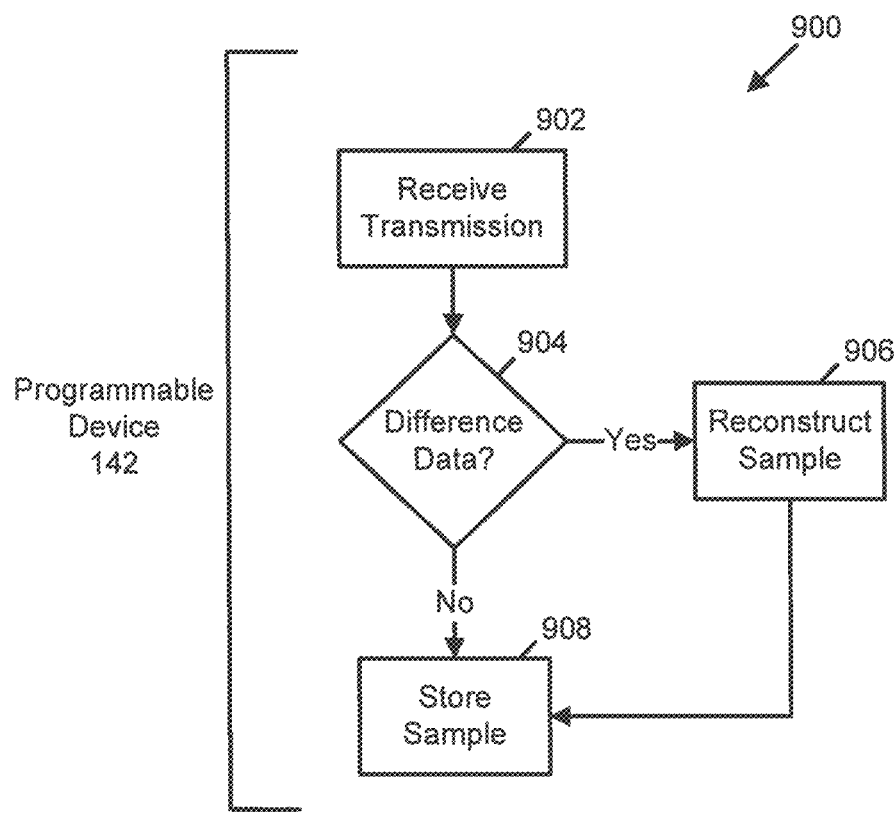
FIG. 9 is a flow diagram illustrating a decompression and recursive data patching process in accordance with an example of the present disclosure.

FIG. 9 illustrates a corresponding patching process 900 executed by the compression component 150 to reconstruct sample received form the compression component 116 during execution of the data differencing process 800. As shown, the patching process 900 starts in act 902 where the compression component 150 receives a transmission, decompresses the transmission (e.g., via Huffman decoding), and stores the decompressed transmission. In act 904, the compression component 150 parses the transmission to determine whether the transmission includes difference data or a sample. If the transmission includes difference data, the compression component 150 reconstructs the sample by patching the previously stored sample with the difference data in act 906. In some examples, patching the previously stored sample using the difference data includes adding the difference data to the data values of previously stored sample and shifting the phase of the sum to the phase of the sample as recorded in the transmission. If the transmission does not include difference data, the compression component 150 proceeds directly to act 908 and stores the sample. After completing the act 908, the compression component 150 returns to the act 902 and receives the next transmission.

Figure 10:
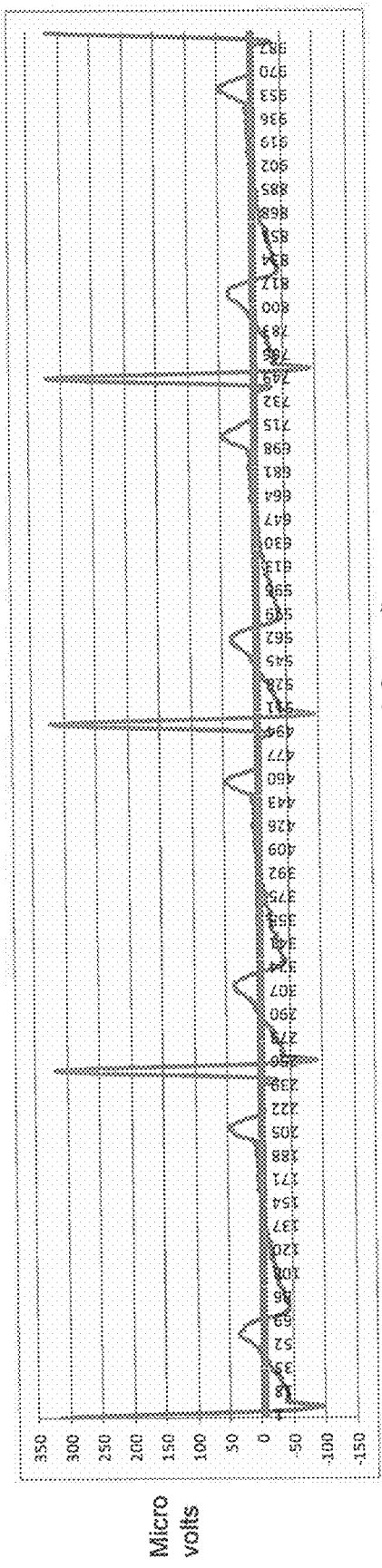
FIG. 10 is a line graph of ECG data recorded by a medical device in accordance with an example of the present disclosure.
Figure 11:
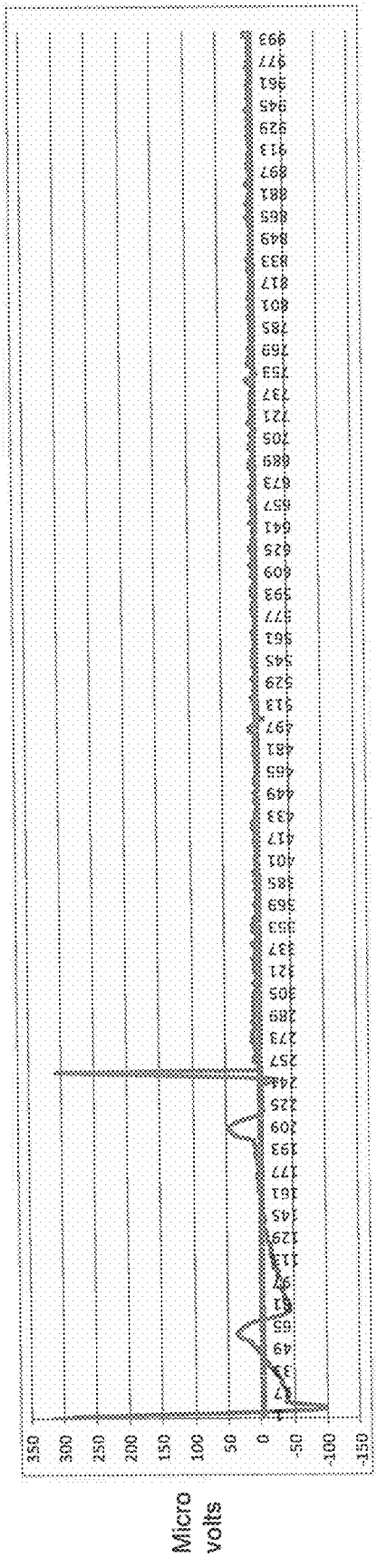
FIG. 11 is a line graph of data to be compressed and transmitted by a compression component in accordance with an example of the present disclosure.

The recursive processing technique described above yields impressive results when applied to ECG data. As one example illustrative of this technique, FIG. 10 illustrates ECG data representative of four heartbeats of a patient recorded by a medical device. FIG. 11 illustrates data transmitted by a compression component configured to execute the data differencing process 800. As shown in FIG. 11, the first heartbeat is transmitted unaltered, but only difference data is transmitted for the second, third and fourth heartbeats. The variance of the difference data is substantially less than the first heartbeat and, therefore, is more readily compressed. While the actual amount of compression will vary between patients (e.g., between 10% to 50%), in this example, the data differencing process 800 resulted in a 27% decrease in the amount of media capacity required to losslessly represent the ECG data. Even greater compression can be expected for ECG data that varies less between heartbeats (such as ECG data representative of asystole).

Multi-Signal Compression

In some examples, the compression component 116 decreases the computing resources required to store and/or transmit patient data by executing a data differencing component configured to identify and transmit differences between two or more physiologic signals descriptive of the same patient activity. For instance, in some examples, the compression component 116 analyzes ECG data acquired from a pair of ECG sensors positioned on the front and back of a patient's thorax to ECG data acquired from a pair of ECG electrodes positioned on the left and right side of the patient's thorax.

Figure 12:
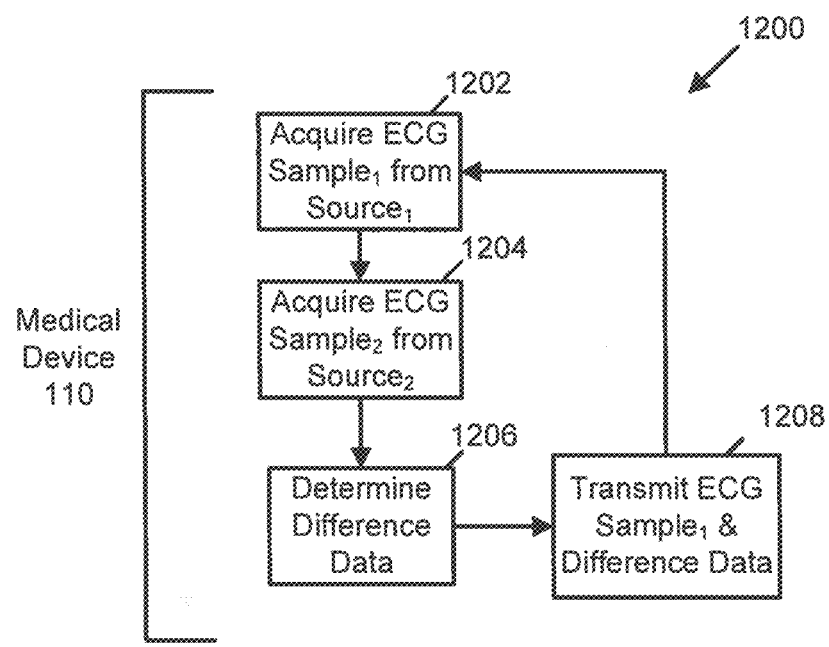
FIG. 12 is a flow diagram illustrating a multi-stream data differencing and compression process in accordance with an example of the present disclosure.

FIG. 12 illustrates a data differencing process 1200 that some examples of the compression component 116 are configured to execute. As shown, the differencing process 1200 starts in the act 1202 with the medical device acquiring a patient data sample$_1$ from a source$_1$ (e.g. front to back pair of electrodes). In act 1204, the medical device acquires a patient data sample$_2$ from a source$_2$ (e.g. side to side pair of electrodes).

In act 1206, the compression component 116 calculates difference data descriptive of the difference between sample$_1$ and sample$_2$. In some examples, calculating this difference data may include aligning the phase of the sample$_2$ to the phase of the sample$_1$ and subtracting data values of the sample$_1$ (e.g., representative of amplitude) from corresponding data values of the sample$_2$. In some examples, the compression component 116 aligns the phase of sample$_1$ to the phase of the sample$_2$ by identifying peaks in the sample$_1$ and the sample$_2$ and aligning the samples so that the peaks overlap. It is appreciated these alignment and subtraction processes may be performed on the sample$_1$ and the sample$_2$ where the samples are transformed into different domains using, for example, a Fourier transform or wavelet transform. In act 1208, the compression component 116 compresses, stores, and/or transmits the sample$_1$ and the difference data to the compression component 150.

For computational efficiency, some examples of the compression component 116 calculate an amount of phase shift using, for example, peak identification as described above and automatically shift samples acquired from the source$_1$ by the amount. In these examples, the compression component 116 monitors a summary of the magnitude of the difference data (e.g., the size of $sample_1$ and the difference data when compressed) and recalculates the amount of phase shift where the magnitude transgresses a configurable threshold.

Figure 13:
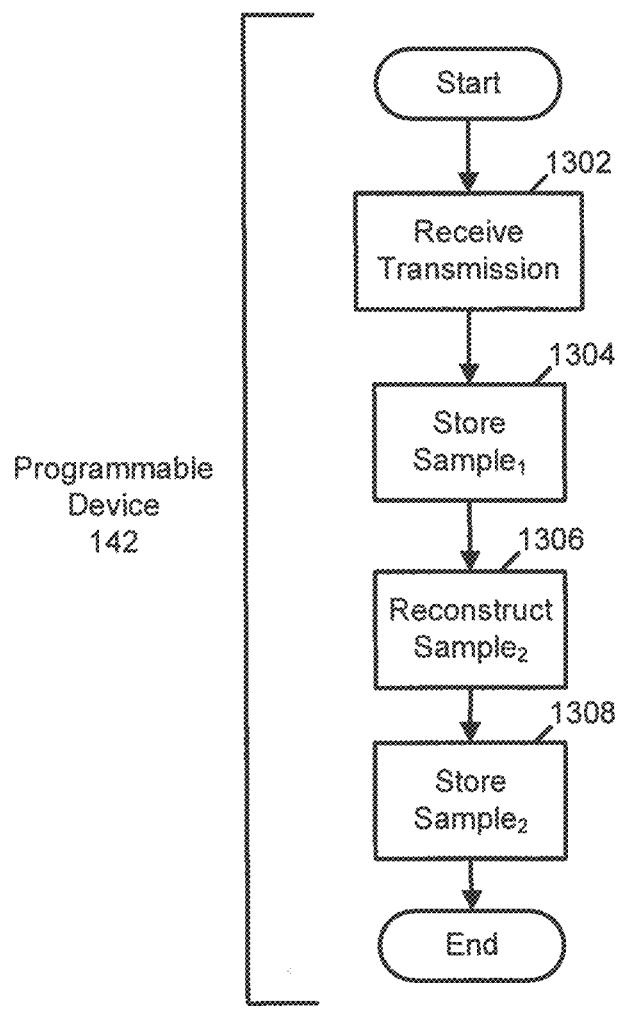
FIG. 13 is a flow diagram illustrating a decompression and multi-stream patching and process in accordance with an example of the present disclosure.

FIG. 13 illustrates a corresponding patching process 1300 executed by the compression component 150 to reconstruct the sample received from the compression component 116 during execution of the data differencing process 1200. As shown, the patching process 1300 starts in act 1302 where the compression component 150 receives a transmission, decompresses the transmission, and stores the decompressed transmission. In act 1304, the compression component 150 parses the transmission and stores the $sample_1$. In act 1306, the compression component 150 reconstructs the $sample_2$ by patching the $sample_1$ with the difference data. In some examples, patching the $sample_1$ using the difference data includes adding the difference data to the data values of the $sample_1$ and shifting the phase of the sum to the phase of the $sample_2$ as recorded in the transmission. In act 1308, the compression component 150 stores the $sample_2$ and the patching process 1300 ends.

In some examples, the multi-signal compression technique may be combined with any of the techniques described above. For instance, in some examples, the $sample_1$ and/or the difference data processed by the differencing process 1200 and the patching process 1300 may be compared to one or more templates stored in the template data store 140 and/or in the data storage 148 as described in the template switching technique. In these examples, differences between the $sample_1$ and/or the difference data and the templates corresponding to each may be compressed and transferred in lieu of the $sample_1$ and/or the difference data, thereby providing greater efficiencies in some situations. In some examples, $sample_1$ and/or the difference data processed by the differencing process 1200 and the patching process 1300 may be compared to previous versions of the $sample_1$ and/or the difference data as described in the recursive processing technique. In these examples, differences between the $sample_1$ and/or the difference data and previous versions of each may be compressed and transferred in lieu of the $sample_1$ and/or the difference data, thereby providing greater efficiencies in some situations.

Figure 14:
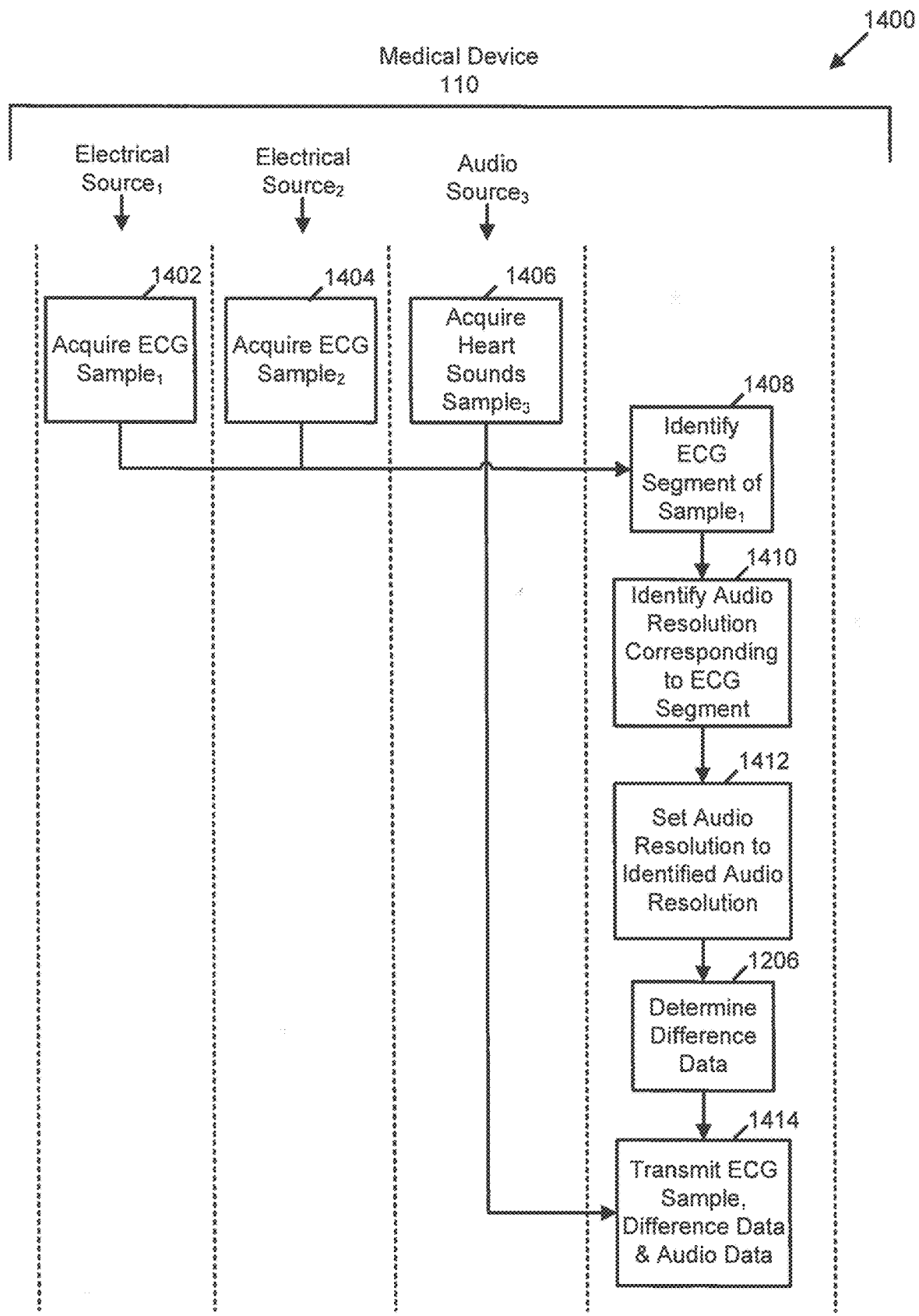
FIG. 14 is a flow diagram illustrating another multi-stream data differencing and compression process in accordance with an example of the present disclosure.

FIG. 14 illustrates another example of data differencing process 1400 that some examples of the compression component 116 are configured to execute. The data differencing process 1400 leverages predefined relationships between physiologic signals to selectively decrease the resolution of recorded data, thereby decreasing the amount of media consumed by the recorded data. As shown, the differencing process 1400 starts in acts 1402, 1404, and 1406 with the medical device 110 acquiring a $sample_1$ of physiologic data from a $source_1$, a $sample_2$ of physiologic data from a $source_2$, and $sample_3$ of physiologic data from a $source_3$. For instance, the $sample_1$ may include ECG data (e.g., derived from the physiologic signals 136) and the $source_1$ may include a front to back pair of ECG sensors (e.g., included in the sensor 128). The $sample_2$ may include ECG data (e.g., derived from the physiologic signals 136) and the $source_2$ may include a side to side pair of ECG sensors (e.g., included in the sensor 128). The $sample_3$ may include heart sounds data (e.g., the physiologic data 160) and the $source_3$ may include an acoustic sensor (e.g., the acoustic sensor 156).

In act 1408, the compression component 116 identifies one or more ECG segments of ECG data recorded in one or more portions of the $sample_1$. Examples of ECG segments include the QRS complex, the P wave, the T wave, the PR interval, the QT interval, the PR segment, and the ST segment. In act 1410, the compression component 116 identifies one or more audio resolutions (e.g., sampling rates and/or discrete sample sizes) associated with each identified ECG segment. These identifications may be executed by referencing a lookup table or other data structure that associates ECG segments with target audio resolutions. This data structure may reside in the data storage 104. In act 1412, the compression component 116 downsamples one or more portions of the $sample_3$ that correspond to the one or more portions of the $sample_1$ according to the identified audio resolutions. The downsampling executed within the act 1412 may include, for example, decreasing the number of bits used to store discrete samples within each portion of $sample_3$ and/or decreasing the number of discrete audio samples stored within each portion of $sample_3$. In act 1206, the compression component 116 calculates difference data descriptive of the difference between $sample_1$ and $sample_2$ as described above with reference to FIG. 12. In act 1414, the compression component 116 compresses, stores, and/or transmits $sample_1$, the difference data, and the downsampled $sample_3$ to the compression component 150.

Figure 15:
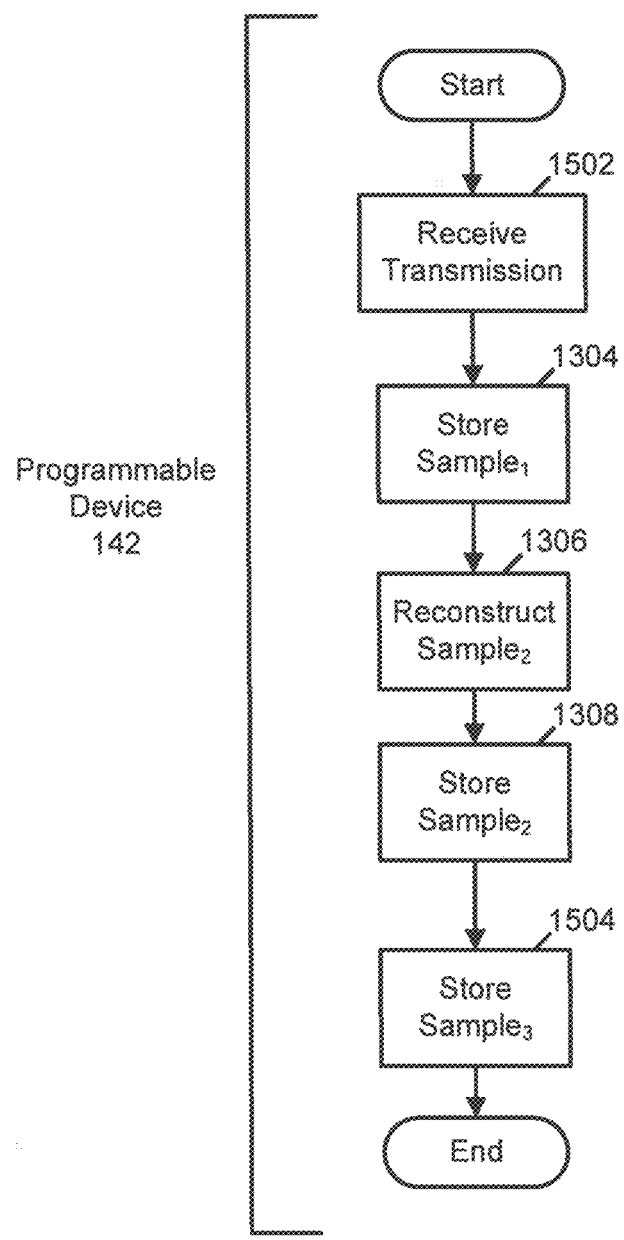
FIG. 15 is a flow diagram illustrating another decompression and multi-stream patching and process in accordance with an example of the present disclosure.

FIG. 15 illustrates a corresponding patching process 1500 executed by the compression component 150 to reconstruct the sample received from the compression component 116 during execution of the data differencing process 1400. As shown, the patching process 1500 starts in act 1502 where the compression component 150 receives a transmission, decompresses the transmission, and stores the decompressed transmission. In acts 1304, 1306, and 1308, the compression component 150 parses the transmission, stores the $sample_1$, reconstructs the $sample_2$ by patching the $sample_1$ with the difference data, and stores the $sample_2$ as described above with reference to FIG. 13. In act 1504, the compression component 150 stores the $sample_3$ and the patching process 1500 ends.

The processes disclosed herein each depict one particular sequence of acts in a particular example. The acts included in these processes may be performed by, or using, one or more programmable devices specially configured as discussed herein. Some acts are optional and, as such, may be omitted in accord with one or more examples. Additionally, the order of acts can be altered, or other acts can be added, without departing from the scope of the systems and methods discussed herein. Furthermore, as discussed above, in at least one example, the acts are performed on a particular, specially configured machine, namely a medical device configured according to the examples disclosed herein.

It is appreciated that the four techniques described above may be combined in various ways to advantageous effect. For example, as described above, the multi-signal compression technique may be combined with either the recursive processing technique or the template switching technique to reduce the amount of media consumed by data descriptive of the any of the samples or difference data described above. In addition, one or more of the template switching technique, the recursive processing technique, and the multi-signal compression may be combined with the selective communication technique to further decrease latency of communications between the medical device 110 and the programmable device 142. Other combinations of the techniques described herein will be apparent in light of this disclosure.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

The invention claimed is:

1. A medical device for efficient transmission of patient data, the medical device comprising:
at least one sensor configured to acquire electrocardiogram (ECG) data descriptive of a patient condition for a patient;
at least one memory configured to store a plurality of ECG templates;
at least one network interface; and
at least one processor coupled to the at least one sensor, the at least one memory, and the at least one network interface, the at least one processor configured to:
receive current ECG data for the patient from the at least one sensor,
compare the current ECG data to a first reference template of the plurality of ECG templates,
calculate difference data between the current ECG data and the first reference template,
compress the difference data and an identifier of the first reference template to generate compressed data, and
transmit the compressed data via the at least one network interface to a programmable device distinct from the medical device.

2. The medical device of claim 1, wherein the at least one processor is further configured to:
receive initial ECG data for the patient from the at least one sensor; and
generate the plurality of ECG templates for the patient based upon the initial ECG data, the plurality of ECG templates stored on the at least one memory.

3. The medical device of claim 2, wherein the at least one processor is further configured to generate the plurality of ECG templates such that the plurality of ECG templates represent a cardiac cycle for the patient at various activity levels, wherein at least one of the plurality of ECG templates is associated with the patient at rest, at least one of the plurality of ECG templates is associated with the patient conducting daily activities, and at least one of the plurality of ECG templates is associated with the patient exercising.

4. The medical device of claim 1, wherein the at least one processor is further configured to determine the first reference template based upon a comparison of the current ECG data and the first reference template.

5. The medical device of claim 4, wherein the at least one processor is configured to determine the first reference template by being further configured to:
compare the current ECG data to each of the plurality of ECG templates to determine a similarity measurement for each of the plurality of ECG templates; and
determine the first reference template based upon the similarity measurements for each of the plurality of ECG templates.

6. The medical device of claim 1, wherein the at least one processor is further configured to:
receive updated ECG data for the patient from the at least one sensor; and
compare the updated ECG data to the first reference template.

7. The medical device of claim 6, wherein the at least one processor is further configured to:
calculate updated difference data between the updated ECG data and the first reference template;
compress the updated difference data and the identifier of the first reference template to generate updated compressed data; and
transmit the updated compressed data via the at least one network interface to the programmable device.

8. The medical device of claim 1, wherein the at least one processor is further configured to:
receive updated ECG data for the patient from the at least one sensor; and
compare the updated ECG data to a second reference template.

9. The medical device of claim 8, wherein the at least one processor is further configured to:
compare the updated ECG data to each of the plurality of ECG templates to determine an updated similarity measurement for each of the plurality of ECG templates; and
determine the second reference template based upon the updated similarity measurement for each of the plurality of ECG templates.

10. The medical device of claim 9, wherein the at least one processor is further configured to:
calculate updated difference data between the updated ECG data and the second reference template;
compress the updated difference data and an identifier of the second reference template to generate updated compressed data; and
transmit the updated compressed data via the at least one network interface to the programmable device.

11. A non-transitory computer-readable medium storing executable instructions to implement a process on a medical device for efficient transmission of patient data, the computer-readable medium comprising instructions to:
receive current ECG data for a patient from at least one sensor;
compare the current ECG data to a first reference template of a plurality of ECG templates;
calculate difference data between the current ECG data and the first reference template;
compress the difference data and an identifier of the first reference template to generate compressed data; and
transmit the compressed data to a programmable device distinct from the medical device.

12. The computer-readable medium of claim 11, further comprising instructions to:
receive initial ECG data for the patient from the at least one sensor; and
generate the plurality of ECG templates for the patient based upon the initial ECG data.

13. The computer-readable medium of claim 12, wherein the instructions to generate the plurality of ECG templates comprise instructions to generate the plurality of ECG templates such that the plurality of ECG templates represent a cardiac cycle for the patient at various activity levels, wherein at least one of the plurality of ECG templates is associated with the patient at rest, at least one of the plurality of ECG templates is associated with the patient conducting daily activities, and at least one of the plurality of ECG templates is associated with the patient exercising.

14. The computer-readable medium of claim 11, further comprising instructions to determine the first reference template based upon a comparison of the current ECG data and the first reference template.

15. The computer-readable medium of claim 14, wherein the instructions to determine the first reference template comprise instructions to:
  compare the current ECG data to each of the plurality of ECG templates to determine a similarity measurement for each of the plurality of ECG templates; and
  determine the first reference template based upon the similarity measurements for each of the plurality of ECG templates.

16. The computer-readable medium of claim 11, further comprising instructions to:
  receive updated ECG data for the patient from the at least one sensor; and
  compare the updated ECG data to the first reference template.

17. The computer-readable medium of claim 16, further comprising instructions to:
  calculate updated difference data between the updated ECG data and the first reference template;
  compress the updated difference data and the identifier of the first reference template to generate updated compressed data; and
  transmit the updated compressed data to the programmable device.

18. The computer-readable medium of claim 11, further comprising instructions to:
  receive updated ECG data for the patient from the at least one sensor; and
  compare the updated ECG data to a second reference template.

19. The computer-readable medium of claim 18, further comprising instructions to:
  compare the updated ECG data to each of the plurality of ECG templates to determine an updated similarity measurement for each of the plurality of ECG templates; and
  determine the second reference template based upon the updated similarity measurement for each of the plurality of ECG templates.

20. The computer-readable medium of claim 19, further comprising instructions to:
  calculate updated difference data between the updated ECG data and the second reference template;
  compress the updated difference data and an identifier of the second reference template to generate updated compressed data; and
  transmit the updated compressed data to the programmable device distinct from the medical device.

* * * * *